(12) United States Patent
Swallow et al.

(10) Patent No.: US 10,429,175 B2
(45) Date of Patent: Oct. 1, 2019

(54) FREQUENCY-BASED DETECTION OF CHEMICAL EXPANSION DYNAMICS IN THIN FILMS

(71) Applicants: Jessica G. Swallow, Cambridge, MA (US); Krystyn J. Van Vliet, Lexington, MA (US); Harry L. Tuller, Wellesley, MA (US); Sean R. Bishop, Silver Spring, MD (US); Jae Jin Kim, Naperville, IL (US); James F. Smith, Denbighshire (GB)

(72) Inventors: Jessica G. Swallow, Cambridge, MA (US); Krystyn J. Van Vliet, Lexington, MA (US); Harry L. Tuller, Wellesley, MA (US); Sean R. Bishop, Silver Spring, MD (US); Jae Jin Kim, Naperville, IL (US); James F. Smith, Denbighshire (GB)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/829,022

(22) Filed: Dec. 1, 2017

(65) Prior Publication Data

US 2018/0156605 A1    Jun. 7, 2018

Related U.S. Application Data

(60) Provisional application No. 62/429,182, filed on Dec. 2, 2016, provisional application No. 62/429,297, filed on Dec. 2, 2016.

(51) Int. Cl.
*G01B 11/16* (2006.01)
*G01B 3/00* (2006.01)
(Continued)

(52) U.S. Cl.
CPC .............. *G01B 11/16* (2013.01); *G01B 3/002* (2013.01); *G01B 5/30* (2013.01); *G01N 21/00* (2013.01); *G01N 27/021* (2013.01); *G01N 29/00* (2013.01)

(58) Field of Classification Search
CPC .......... G01B 11/16; G01B 3/002; G01B 5/30; G01N 21/00; G01N 29/00
(Continued)

(56) References Cited

U.S. PATENT DOCUMENTS 4,148,587 A * 4/1979 Erdmann ............... G01B 11/24
                                                     250/201.4
7,453,560 B2 * 11/2008 Miyake .................. G03F 7/706
                                                     250/492.1
(Continued)

OTHER PUBLICATIONS

Kim, S.-W. et al., Thickness-profile measurement of transparent thin-film layers by white-light scanning interferometry, Applied Optics 1999, 38, 5968-5973.
(Continued)

*Primary Examiner* — Roy M Punnoose
(74) *Attorney, Agent, or Firm* — Smith Baluch LLP

(57) ABSTRACT

Current techniques for measuring chemical expansion in thin film structures are too slow, too imprecise, or require synchrotrons. In contrast, nanoscale electrochemomechanical spectroscopy (NECS) can be used to make nanoscale measurements at time scales of seconds with simple contact or non-contact sensors. In a NECS measurement, a sample, such as thin-film oxide structure, is subjected to a temporally modulated stimulus, such as a sinusoidally alternating voltage. The stimulus causes the sample to expand, contract, deflect, or otherwise deform. A sensor, such as a contact probe or optical sensor, produces an electrical signal in response to this deformation that is correlated with the temporal modulation of the stimulus. Because the stimulus
(Continued)

and deformation are correlated, the temporal modulation of the stimulus can be used to filter the deformation signal produced by the sensor, producing a precise, sensitive measurement of the deformation.

19 Claims, 11 Drawing Sheets

(51) Int. Cl.
    *G01B 5/30* (2006.01)
    *G01N 27/02* (2006.01)
    *G01N 29/00* (2006.01)
    *G01N 21/00* (2006.01)

(58) Field of Classification Search
    USPC .................................................. 356/32, 601
    See application file for complete search history.

(56) References Cited

U.S. PATENT DOCUMENTS

| | | | | |
|---|---|---|---|---|
| 8,394,026 | B2* | 3/2013 | Eskandari | A61B 8/00 600/438 |
| 2003/0020923 | A1* | 1/2003 | Dubois | G01B 11/164 356/502 |
| 2009/0249881 | A1* | 10/2009 | Nitecki | G01F 1/3281 73/706 |
| 2014/0127508 | A1* | 5/2014 | Saif | B01L 3/502707 428/401 |
| 2015/0308923 | A1* | 10/2015 | Chin | G01D 5/35364 356/73.1 |

OTHER PUBLICATIONS

Kim, Y.-M. et al., Probing oxygen vacancy concentration and homogeneity in solid-oxide fuel-cell cathode materials on the subunit-cell level, Nature Materials 2012, 11, 888-894.
Korobko, R. et al., Giant electrostriction in Gd-doped ceria, Adv. Mater. 2012, 24, 5857-5861.
Korobko, R. et al., In-situ extended X-ray absorption fine structure study of electrostriction in Gd doped ceria, Appl. Phys. Lett. 2015, 106, 042904-5.
Koyoma, Y. et al., Harnessing the actuation potential of solid-state intercalation compounds, Adv. Funct. Mater. 2006, 16, 492-498.
Kuhn, M. et al., Oxygen nonstoichiometry and defect chemistry of perovskite-structured $Ba_xSr_{1-x}Fe_yO_{3-y/2+\delta}$, Chem. Mater. 2013, 25, 2970-2975.
Kumar, A. et al., Measuring oxygen reduction/evolution reactions on the nanoscale, Nature Chemistry 2011, 3, 707-713.
Kumar, A. et al., Spatially Resolved Mapping of Oxygen Reduction/Evolution Reaction on Solid-Oxide Fuel Cell Cathodes with Sub-10 nm Resolution, ACS Nano 2013, 7, 3808-3814.
Kurosaki, K. et al., Nanoindentation tests for TiO2, MgO, and YSZ single crystals, Journal of Alloys and Compounds 2005, 386, 261-264.
Kushi, T. et al., Elastic modulus and internal friction of SOFC electrolytes at high temperatures under controlled atmospheres, J. Power Sources 2011, 196, 7989-7993.
Lai, W. et al., Impedance spectroscopy as a tool for chemical and electrochemical analysis of mixed conductors: A case study of ceria, J. Am. Ceram. Soc. 2005, 88, 2979-2994.
Lu, Q. et al., Voltage-controlled topotactic phase transition in thin-film $SrCoO_x$ monitored by in situ X-ray diffraction, Nano Letters 2016, 16, 1186-1193.
Maloney, J. M. et al., Mechanical fluidity of fully suspended biological cells, Biophys. J. 2013, 106, 1767-1777.
Manning, P. S. et al., Oxygen self-diffusion and surface exchange studies of oxide electrolytes having the fluorite structure, Solid State Ionics 1997, 93, 125-132.

Marrocchelli, D. et al., Understanding chemical expansion in non-stoichiometric oxides: ceria and zirconia case studies, Adv. Funct. Mater. 2012, 22, 1958-1965.
McIntosh, S. et al., Oxygen stoichiometry and chemical expansion of $Ba_{0.5}Sr_{0.5}Co_{0.8}Fe_{0.2}O_{3-\delta}$ measured by in situ neutron diffraction, Chem. Mater. 2006, 18, 2187-2193.
Moreno, R. et al., Chemical strain kinetics induced by oxygen surface exchange in epitaxial films explored by time-resolved x-ray diffraction, Chem. Mater. 2013, 25, 3640-3647.
Nakayama, M. et al., A first-principles study on phase transition induced by charge ordering of Mn3+/Mn4+ in spinel $LiMn_2O_4$, Solid State Commun. 2010, 150, 1329-1333, ISSN 0038-1098.
Park, K. et al., Fast performance degradation of SOFC caused by cathode delamination in long-term testing, International Journal of Hydrogen Energy 2010, 35, 8670-8677.
Paulsen, J. M. et al., Phase Diagram of Li—Mn—O Spinel in Air, Chem. Mater. 1999, 11, 3065-3079.
Perry, N. H. et al., Defect chemistry and surface oxygen exchange kinetics of La-doped Sr(Ti, Fe)O3-α in oxygen-rich atmospheres, Solid State Ionics 2015, 273, 18-24.
Perry, N. H., Strongly coupled thermal and chemical expansion in the perovskite oxide system $Sr(Ti,Fe)O_{3-\alpha}$, J. Mater. Chem. A 2015, 3, 3602-3611.
Rothschild, A. et al., Electronic structure, defect chemistry, and transport properties of $SrTi_{1-x}Fe_xO_{3-y}$, Chem. Mater. 2006, 18, 3651-3659.
Sato, K. et al., Fracture process of nonstoichiometric oxide based solid oxide fuel cell under oxidizing/reducing gradient conditions, J. Power Sources 2010, 195, 5481-5486.
Sethuraman, V. A. et al., Realtime stress measurements in lithium-ion battery negative-electrodes, J. Power Sources 2012, 206, 334-342.
Sheldon, B. W. Sheldon et al., Grain boundary induced compositional stress in nanocrystalline ceria films, Solid State Ionics 2013, 233, 38-46.
Sherrit, S., Smart material/actuator needs in extreme environments in space, Proceedings of the SPIE Smart Structures Conference 2005, 13 pages.
Sheth, J. et al., Coupling of strain, stress, and oxygen non-stoichiometry in thin film $Pr_{0.1}Ce_{0.9}O_{2-\delta}$, Nanoscale 2016, 8, 16499-16510.
Sheth, J. et al., In Situ Stress Evolution in $Li_{1+x}Mn_2O_4$ Thin Films during Electrochemical Cycling in Li-Ion Cells, J. Electrochem. Soc. 2016, 163, A2524-A2530.
Simmons, R. O. et al., Measurement of equilibrium vacancy concentrations in aluminum, Phys. Rev. 1960, 117, 52-61.
Sinclair, R., In situ high-resolution transmission electron microscopy of material reactions, MRS Bull. 2013, 38, 1065-1071.
Songtao, H. et al., Structural and electrochemical properties of Li(+) and Co(3+)-codoped $LiMn_2O_4$, Chinese Journal of Rare Materials 2006, 30, 129-133—English language Abstract.
Soni, S. K. et al., Thickness effects on the lithiation of amorphous silicon thin films, Scripta Materialia 2011, 64, 307-310.
Swallow, J. G. et al., Dynamic chemical expansion of thin-film non-stoichiometric oxides at extreme temperatures, Nature Materials 2017, 23, 749, 7 pages.
Swallow, J. G. et al., Operando reduction of elastic modulus in (Pr, Ce)$O_{2-\delta}$ thin films, Acta Materialia 2016, 105, 16-24.
Tomkiewicz, A. C. et al., Evidence for low oxygen stoichiometry of cubic $Ba_{0.5}Sr_{0.5}Co_{0.5}Fe_{0.5}O_{3-67}$ from in-situ neutron diffraction, Solid State Ionics 2013, 253, 27-31.
Tsvetkov, N. et al., Accelerated oxygen exchange kinetics on $Nd_2NiO_{4+\delta}$ thin films with tensile strain along c-axis, ACS Nano 2016, 9, 1613-1621.
Tuller, H. L. et al., Point defects in oxides: tailoring materials through defect engineering, Annu. Rev. Mater. Res. 2011, 41, 369-398.
Van Der Ven, A. et al., Phase transformations and volume changes in spinel $Li_{1+x}Mn_2O_4$, Solid State Ionics 2000, 135, 21-32.
Waldbilig, D. et al., Electrochemical and microstructural characterization of the redox tolerance of solid oxide fuel cell anodes, J. Power Sources 2005, 145, 206-215.

(56) References Cited

OTHER PUBLICATIONS

Xia, Y. et al., An investigation of lithium ion insertion into spinel structure Li—Mn—O compounds, J. Electrochem. Soc. 1996, 143, 825-833.
Zhang, S. et al., Piezoelectric materials for high temperature sensors, J. Am. Ceram. Soc. 2011, 94, 3153-3170.
Abazari, M. et al., High-temperature electrical conductivity measurements on nanostructured yttria-doped ceria thin films in ozone, J. Am. Ceram. Soc. 2011, 95, 312-317.
Amezawa, K. et al., Elastic moduli of $Ce_{0.9}Gd_{0.1}O_{2-\delta}$ at high temperatures under controlled atmospheres, Solid State Ionics 2011, 198, 32-38.
Amrhein, M. et al., Design of a high-temperature utility electromechanical actuator, SAE Technical Paper 2012, 11 pages.
Atkinson, A. et al., Chemically-induced stresses in ceramic oxygen ion conducting membranes, Solid State Ionics 2000, 129, 259-269.
Balke, N. et al., Nanoscale mapping of ion diffusion in a lithium-ion battery cathode, Nature Nanotech. 2010, 5, 749-754.
Bergerhoff, G. et al., The inorganic crystal structure data base, Journal of Chemical Information and Computer Sciences 1983, 23, 66-69.
Bishop, S. R. et al., Chemical expansion of nonstoichiometric $Pr_{0.1}Ce_{0.9}O_{2-\delta}$: Correlation with defect equilibrium model, J. Eur. Ceram. Soc. 2011, 31, 2351-2356.
Bishop, S. R. et al., Chemical expansion: Implications for electrochemical energy storage and conversion devices, Annu. Rev. Mater. Res. 2014, 44, 205-239.
Bishop, S. R. et al., Defects and transport in $PrxCe_{1-x}O_{2-\delta}$: Composition trends, J. Mater. Res. 2012, 27, 2009, 8 pages.
Bishop, S. R. et al., Electrical conductivity and defect equilibria of $Pr_{0.1}Ce_{0.9}O_{2-\delta}$, Phys. Chem. Chem. Phys. 2011, 13, 10165-10173.
Bishop, S. R. et al., Impact of size scale on electro-chemo-mechanical coupling properties in MIECs: Bulk and thin film (Pr, Ce)$O_{2-\delta}$, ECS Trans. 2014, 61, 31-36.
Borisevich, A. Y. et al., Functional electron microscopy for electrochemistry research: From the atomic to the micro scale, The Electrochemical Society Interface 2014, 61-66.
Bowman, W. J. et al., Measuring bandgap states in individual non-stoichiometric oxide nanoparticles using monochromated STEM EELS: The Praseodymium-ceria case, Ultramicroscopy 2016, 167, 5-10.
Chason, E. et al., Monitoring stress in thin films during processing, Surface Engineering 2013, 19, 387-391.
Chen, D. et al., Non-stoichiometry in oxide thin films: A chemical capacitance study of the praseodymium-cerium oxide system, Adv. Funct. Mater. 2013, 23, 2168-2174.
Chen, D. et al., Praseodymium-cerium oxide thin film cathodes: Study of oxygen reduction reaction kinetics, J. Electroceram. 2012, 28, 62-69.
Chen, D. et al., Voltage-controlled nonstoichiometry in oxide thin films: $Pr_{0.1}Ce_{0.9}O_{2-\delta}$ case study, Adv. Funct. Mater. 2014, 24, 7638-7644.
Chen, D., "Characterization and Control of Non-stoichiometry in $Pr_{0.1}Ce_{0.9}O_{2-\delta}$ thin films: Correlation with SOFC Electrode Performance," Doctoral Thesis, Massachusetts Institute of Technology, Jun. 2014, 100 pages.
Chen, Q. N. et al., Imaging space charge regions in Sm-doped ceria using electrochemical strain microscopy, Appl. Phys. Lett. 2014, 105, 201602-4.
Chen, Y. et al., Impact of Sr segregation on the electronic structure and oxygen reduction activity of $SrTi_{1-x}Fe_xO_3$ surfaces, Energy Environ. Sci. 2012, 5, 7979-7988.
Cheng, C. et al., Reversible electrochemical actuation of metallic nanohoneycombs induced by pseudocapacitive redox processes, ACS Nano 2015, 9, 3984-3995.
Damjanovic, D., Materials for high temperature piezoelectric transducers, Current Opinion in Solid State and Materials Science 1998, 3, 469-473.
Egerton, R. F. et al., Electron energy-loss spectroscopy in the TEM, Rep. Prog. Phys. 2008, 72, 016502, 25 pages.
Endres, P. et al., Influence of processing on the Li:Mn ratio in spinel phases of the system $Li_{1+x}Mn_{2-x}O_{4-\delta}$, Solid State Ionics 1996, 89, 221-231.
Feng, X. et al., On the Stoney formula for a thin film-substrate system with nonuniform substrate thickness, Transactions of the ASME 2007, 74, 1276-1281.
Gelhaus, F. E. et al., Robot applications in nuclear power plants, Progress in Nuclear Energy 1990, 23, 1-33.
Gong, C. et al., Spatially dependent lattice deformations for dislocations at the edges of graphene, ACS Nano 2015, 9, 656-662.
Grande, T. et al., Anisotropic thermal and chemical expansion in Sr-substituted LaMnO3+δ: Implications for chemical strain relaxation, Chem. Mater. 2012, 24, 338-345.
Hailstone, R. K. et al., A study of lattice expansion in $C_eO_2$ nanoparticles by transmission electron microscopy, J. Phys. Chem. C 2009, 113, 15155-15159.
Hiraiwa, C. et al., Chemical expansion and change in lattice constant of Y-doped $BaZrO_3$ by hydration/ dehydration reaction and final heat-treating temperature, J. Am. Ceram. Soc. 2013, 96, 879-884.
Hopper, E. M. et al., Oxygen exchange in $La_{0.6}Sr_{0.4}CO_{0.2}Fe_{0.8}O_{3-\delta}$ thin-film heterostructures under applied electric potential, J. Phys. Chem. C 2015, 119, 19915-19921.
Huang, Z. et al., Grain rotation and lattice deformation during photoinduced chemical reactions revealed by in situ X-ray nanodiffraction, Nature Materials 2015, 14, 691, 6 pages.
Hytch, M. J. et al., Quantitative measurement of displacement and strain fields from HREM micrographs, Ultramicroscopy 1998, 74, 131-146.
Irvine, J. T. S. et al., A. R. West, Electroceramics: Characterization by impedance spectroscopy, Adv. Mater. 2004, 2, 132-138.
Jain, A. et al., The Materials Project: A materials genome approach to accelerating materials innovation, APL Materials 2013, 1, 011002-11.
Jamnik, J. et al., Generalized equivalent circuits for mass and charge transport: Chemical capacitance and its implications, Phys. Chem. Chem. Phys. 2001, 3, 1668-1678.
Jang, J. H. et al., In situ observation of oxygen vacancy dynamics and ordering in the epitaxial $LaCoO_3$ system, ACS Nano 2017, 11, 6942-6949.
Jung, W. et al., Investigation of nanoporous platinum thin films fabricated by reactive sputtering: Application as micro-SOFC electrode, J. Power Sources 2015, 275, 860-865.
Kalinin, S. V. et al., Local electrochemical functionality in energy storage materials and devices by scanning probe microscopies: status and perspectives, Adv. Mater. 2010, 22, E193-E209.
Kawada, T. et al., Determination of oxygen vacancy concentration in a thin film of La0.6Sr0.4CoO3−δ by an electrochemical method, J. Electrochem. Soc. 2002, 149, E252-E259.
Kim, J. J. et al., Investigation of nonstoichiometry in oxide thin films by simultaneous in situ optical absorption and chemical capacitance measurements: Pr-doped ceria, a case study, Chem. Mater. 2014, 26, 1374-1379.

\* cited by examiner

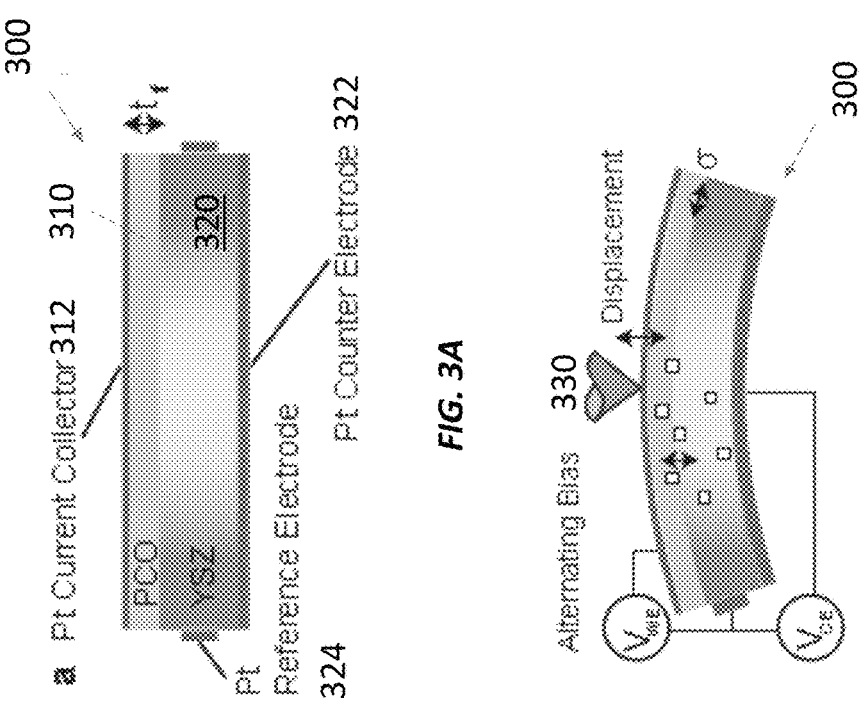
FIG. 3C
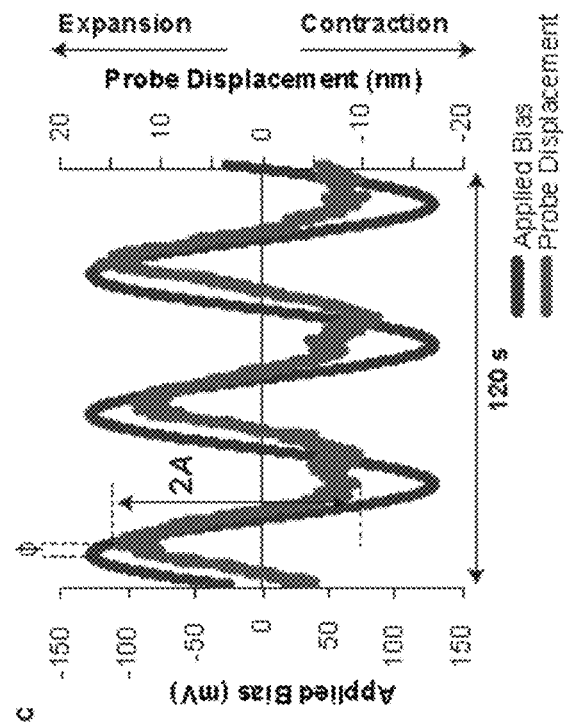
FIG. 3A
FIG. 3B

FREQUENCY-BASED DETECTION OF CHEMICAL EXPANSION DYNAMICS IN THIN FILMS

CROSS-REFERENCE TO RELATED APPLICATION(S)

This application claims the priority benefit, under 35 U.S.C. § 119(e), of U.S. Application No. 62/429,297, which is entitled "Dynamic Chemical Expansion of Thin Film Non-Stoichiometric Oxides at Extreme Temperature," and was filed on Dec. 2, 2016, and of U.S. Application No. 62/429,182, which is entitled "Frequency-Based Approach to Detecting Chemical Expansion Dynamics in Thin Films" and was also filed on Dec. 2, 2016. Each of these applications is incorporated herein by reference in its entirety.

GOVERNMENT SUPPORT

This invention was made with Government support under Grant No. DE-SC0002633 awarded by the Department of Energy. The Government has certain rights in the invention.

BACKGROUND

Chemical expansion has significant potential for producing stress, fracture, and strain during high temperature electrochemical device operation. This may have a negative functional impact, leading to cracking or delamination in situ, or it may be turned to a more positive outcome by tuning material performance through mechanical cues including stress and strain. Being able to take advantage of chemical expansion operando while avoiding detrimental mechanical failures fundamentally requires the ability to detect such effects under in situ conditions. This includes characterizing oxides in both equilibrium conditions and dynamic conditions that might represent, for example, gas interruption or redox cycling. Additionally, given the differences known to exist between film and bulk forms of these oxides, thin film-specific characterization methods are required.

There are several ways to characterize chemical expansion. Among these, the most prominent are diffraction-based techniques and dilatometry. Diffraction has many advantages, including a diversity of in situ measurement possibilities and the flexibility to measure films, powders, or pellets and determine orientation-specific information. However, most diffraction instruments require a minimum of ten seconds to achieve a usable signal-to-noise ratio (SNR) threshold, meaning that faster measurements are not possible without the aid of a synchrotron. Furthermore, while diffraction is sensitive to lattice strain or phase changes, it cannot detect new lattice site formation or volume change that is not periodic (e.g., that might be associated with grain boundaries, dislocations, or similar defects).

In contrast, dilatometry is a fairly straightforward type of measuring volume changes caused by a physical or chemical process. For example, a material undergoing chemical expansion may push a rod connected to a strain gauge, causing a change in the strain measured by the strain gauge. Dilatometry is sensitive, on sub-second time scales, to all types of volume change. Unfortunately, dilatometry is better suited to studying bulk samples than to studying thin films.

SUMMARY

The present technology includes methods and systems for characterizing devices, e.g., by detecting chemical expansion on sub-second time scales in situ without a synchrotron. Examples of these methods comprises applying a time-varying stimulus to the device, such as a device with an oxide film. This time-varying stimulus causing a time-varying change in gas content of the device (e.g., oxygen content of an oxide film). These example methods also include measuring a time-varying deformation of the device caused by the time-varying change in gas content of the device. If desired, the device may be kept at a temperature of at least about 450 degrees Celsius while applying the time-varying stimulus.

In some cases, applying the time-varying stimulus to the device comprises applying an alternating bias voltage to the device. This alternating bias voltage may vary a rate of about 0.01 Hz to about 1 Hz. In some cases, a clamp constrains the device's in-plane expansion while the device is subject to the time-varying voltage.

Measuring the time-varying deformation may comprise sensing displacement of a probe in contact with a surface of the device, measuring an out-of-plane chemical expansion, measuring a deflection due to interfacial stress, or any combination thereof.

Example methods may also include filtering a signal representing the time-varying deformation based on a spectral component of the time-varying stimulus (e.g., the alternation frequency of an alternating bias voltage). If desired, a processor may determine an amplitude of the time-varying deformation, a phase difference between the time-varying deformation and the time-varying stimulus, or both.

Other embodiments of the present technology include systems for characterizing a device. An example system may comprising a stimulus source and a sensor. The stimulus source is configured to apply a time-varying stimulus to the device. This time-varying stimulus causing a time-varying change in gas content of the device. And the sensor is configured to measure a time-varying deformation of the device caused by the time-varying change in gas content of the device.

In some cases, the stimulus source comprises a voltage source configured to apply an alternating bias voltage to the device. This voltage source may vary the alternating bias voltage at a rate of about 0.01 Hz to about 1 Hz.

In some cases, the sensor comprises a probe in contact with a surface of the device. In other cases, the sensor comprises a light source configured to illuminate a surface of the device and a detector configured to detect light reflected off the surface of the device. The sensor may be configured to measure an out-of-plane chemical expansion of the device, a deflection of the device due to interfacial stress, or both.

The system may also include a heater configured to keep the device at a temperature of at least about 450 degrees Celsius during application of the time-varying stimulus. And it can include circuitry, such as a lock-in amplifier or processor, in electrical communication with the sensor, to filter a signal representing the time-varying deformation based on a spectral component of the time-varying stimulus.

Yet another embodiment of present technology includes a method of characterizing a device comprising an oxide film. This method comprising heating the device to a temperature of at least 450 degrees Celsius. When the device is at this temperature, a stimulus source applies a time-varying voltage to the device. This time-varying voltage causing a time-varying change in oxygen content of the oxide film. A probe in contact with a surface of the device measure a time-varying deformation of the device caused by the time-varying change in oxygen content of the oxide film. And a processor or other circuitry operably coupled to the probe determines an amplitude of the time-varying deformation and a phase difference between the time-varying deformation and the time-varying stimulus.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTIONS OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 3A shows an oxide thin film sample with electrodes for a NECS measurement.

FIG. 3B shows a contact displacement measurement of the oxide thin film sample of FIG. 3A while subject to an alternating bias.

FIG. 3C shows a plot of applied bias and probe displacement versus time for the NECS measurement of FIG. 3B.

DETAILED DESCRIPTION

Figure 1:
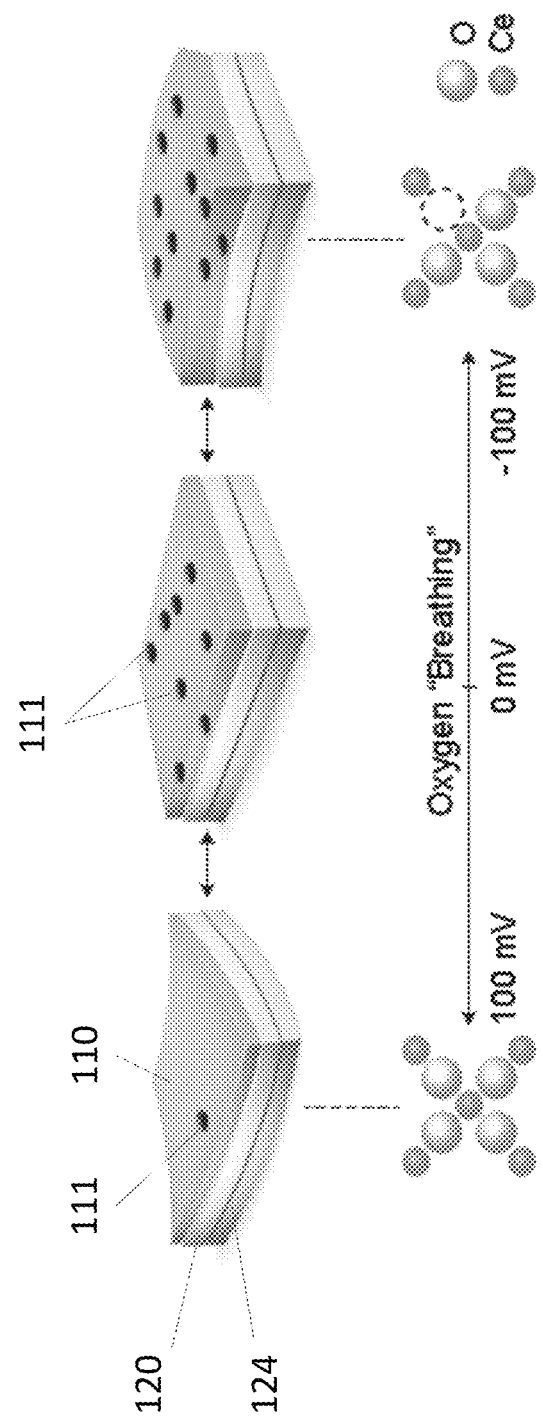
FIG. 1 illustrates the "electrochemical breathing" process that occurs during direct chemical expansion and can be measured with nanoscale electrochemomechanical spectroscopy (NECS).

Nanoscale electrochemical spectroscopy (NECS) can combine the simplicity of dilatometry with the flexibility of diffraction in a standard laboratory setting. NECS directly measures displacement, rather than lattice parameter changes as would be characterized by diffraction, and can be adapted depending on sample design to detect stress-amplified actuation or pure film strain on the scale of nanometer, including at operando high temperatures and gas environments. NECS can also be used to estimate changes in activation energy and breathing mechanisms in these or other functional oxide films (e.g., battery cathode materials) and multilayers as a function of composition or extreme environment, including the potential for spatially resolved mapping. NECS also provides quantitative insights into the dynamic mechanical response of such materials to electrochemical driving forces, and should facilitate new understanding of materials and conditions that increase or decrease stress, strain, and fracture under redox cycling or gas interruption for applications in fuel cells, electrolyzers, catalysis, or gas sensors, or in response to electrical signals or environmental stimuli for sensor or actuator applications.

NECS has several advantages over existing techniques to measure film expansion. First, it is more versatile and accessible than any one alternative approach. Second, unlike curvature-based methods, NECS can be applied to measure both strain-only displacement and displacements amplified by substrate deflection. Third, unlike interferometry-based measurements, NECS requires no particular knowledge of the optical properties of samples, nor does it require samples to have specific optical properties (e.g., reflectivity) as are required for many curvature-based techniques. Fourth, unlike diffraction-based chemical expansion measurements, NECS can measure displacements and volumetric expansion resulting from mechanisms other than lattice strain (e.g., grain boundary mediated effects). Fifth, NECS can achieve second-scale temporal resolution for lattice-strain-based displacements without the aid of a synchrotron used in x-ray diffraction or neutron diffraction (methods that can also include potentially damaging high energy radiation), and may be able to achieve faster temporal resolutions with additional modification of instrumentation and software.

And sixth, unlike dilatometry, NECS can be applied to thin film samples, and has improved spatial resolution as compared to most dilatometers.

Chemical Expansion Caused by Electrically Pumping Gas (Oxygen)

NECS is enabled, at least in part, by the chemical expansion, which is coupling between material volume and point defect concentration. In a $Pr_xCe_{1-x}O_{2-\delta}$ (PCO) film, chemical expansion occurs when an oxygen vacancy is formed according to the following equation:

$$2Pr_{Ce}^x + O_O^x \leftrightarrow 2Pr'_{Ce} + V^{**}_O + \tfrac{1}{2}O_{2(g)} \tag{1}$$

where $Pr_{Ce}^x$ and $Pr'_{Ce}$ denote $Pr^{4+}$ and $Pr^{3+}$, respectively, on Ce sites; $O_O^x$ denotes $O^{2-}$ on an oxygen site; and $V^{**}_O$ denotes a vacancy on an oxygen site in the PCO film.

Electrically pumping oxygen out of a PCO film causes the PCO film to expand. This can be seen by writing out the mass action relation for Eq. (1), where $\Delta H_{r,Pr}$ is the enthalpy of reaction, $k_{r,Pr}$ is a pre-exponential term, and $K_{r,Pr}$ is the equilibrium constant of this reaction:

$$\frac{[Pr'_{Ce}]^2[V_O^{\cdot\cdot}]pO_2^{1/2}}{[Pr_{Ce}^x]^2[O_O^x]} = k_{r,Pr}\exp\left(\frac{-\Delta H_{r,Pr}}{kT}\right) = K_{r,Pr} \tag{2}$$

In Eq. 2, $pO_2$ is the partial oxygen pressure, k is Boltzman's constant, and T is the temperature. In an electrochemical system, the oxygen vacancy concentration $[V^{**}_O]$ is determined based on the effective chemical potential of oxygen $\mu_{O_2,eff}$, which can be shifted away from the chemical potential of oxygen in the gas phase, $\mu_{O_2,g}$, by an electrical bias $\Delta E$ according to the Nernst relation:

$$\mu_{O_2,eff} = \mu_{O_2,g} + 4e\Delta E \tag{3}$$

Thus, for an oxide film that is electrically biased relative to a reference state in equilibrium with a gas phase, there is an effective oxygen partial pressure $pO_{2,eff}$:

$$p_{O_2,eff} = p_{O_2,g}\exp\left(\frac{4e\Delta E}{kT}\right) \tag{4}$$

Chemical capacitance is defined as the chemical storage capacity of a material under a potential, and results from formation and annihilation of oxygen vacancies and $Pr'_{Ce}$ in PCO. Equation 5 relates chemical capacitance $C_{chem}$ to $pO_{2,eff}$, film volume $V_{film}$, and $[V^{**}_O]$:

$$C_{chem} = -\frac{8e^2 V_{film}}{kT}\left(pO_{2,eff}\frac{\delta[V_O^{\cdot\cdot}]}{\delta pO_{2,eff}}\right) \tag{5}$$

By rearranging Eq. 5 and integrating with respect to $pO_{2,eff}$, $[V^{}_O]$ may be determined if a reference state $pO_{2,eff}$ is available for which $[V^{}_O]$ is known. This results in Eq. 6:

$$[V_O^{\cdot\cdot}](pO_{2,eff}) = \frac{kT}{8e^2 V_{film}}\int C_{chem} d\ln pO_{2,eff} + [V_O^{\cdot\cdot}](pO_{2,eff}) \tag{6}$$

In the high $pO_2$ regime, solving the above equation gives a linear relationship between chemical capacitance and $[V^{**}_O]$. This result has been well-established through prior electrochemical measurements coupled to defect modeling for PCO.

One consequence of the above result is that an electrical bias can be used to pump oxygen into and out of a PCO film grown on an ionically conducting substrate. This "electrochemical breathing" enables instantaneous adjustment of an oxide's equilibrium $[V^{**}_O]$ or $\delta$, meaning that all coupled effects (including volume change through chemical expansion) may also be driven rapidly via electrical modulation. In principle the same approach can be used to pump oxygen or other mobile ionic species into or out of any conducting oxide so long as leakage currents (e.g., due to gas-phase reactions) are reduced or minimized.

FIG. 1 illustrates the "electrochemical breathing" process that occurs during direct chemical expansion. An oxide film 110 on an oxide ion conducting substrate 120 is biased with respect to a reference electrode 124, oscillating between cathodic (negative, reducing) and anodic (positive, oxidizing) conditions. Under anodic bias, the film 110 breathes oxygen in, producing an overall contraction and reduction in film thickness and corresponding negative substrate deflection. Under cathodic bias, the film 110 releases oxygen, resulting in increased oxide ion vacancy content (indicated by dark holes 111) and a corresponding increase in film thickness and positive substrate deflection.

Measuring Film Breathing and Mechanical Deflection in Oxide Films

Figure 2A:
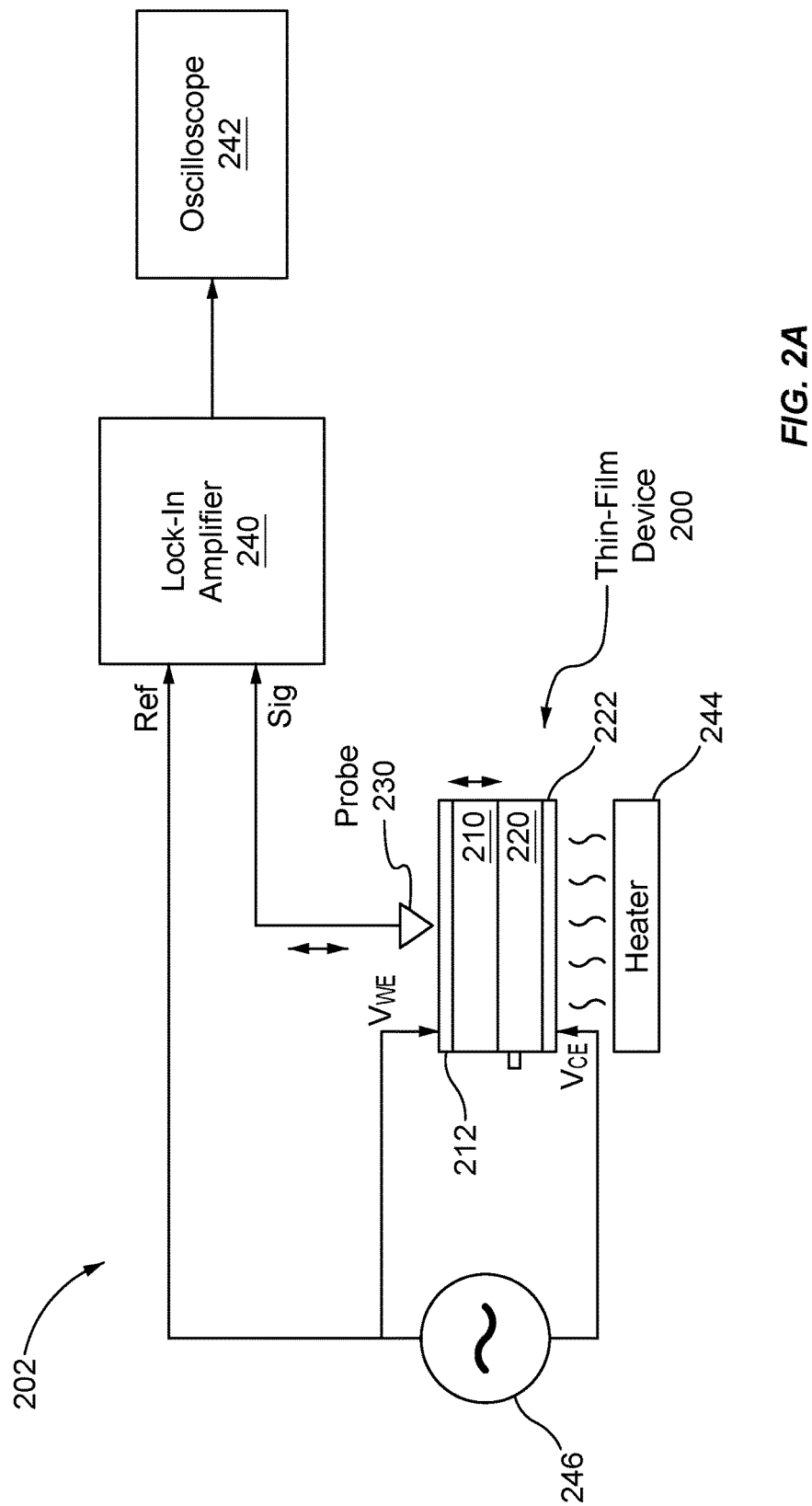
FIG. 2A shows a system for NECS of fuel cells, batteries, sensors, actuators, and other devices susceptible to chemical expansion.

FIG. 2A illustrates a nanoscale electrochemomechanical spectroscopy (NECS) system 202 for quantifying film "breathing" and mechanical deflection in an thin-film device 200, such as a fuel cell, battery, sensor, or actuator, due to reversible oxygen uptake. The NECS system 202 applies a temporally modulated stimulus, such as electrical bias or temperature, to the thin-film device 200 and measures the resulting time-varying, nanoscale changes in displacement or thickness experienced by the thin-film device 200. It processes these measurements to produce information about the oxide film device's susceptibility to stress, fracture, or strain due to chemical expansion at high temperature.

The NECS system 202 shown in FIG. 2A includes a voltage source 246 that applies a temporally modulated bias voltage to the thin-film device 200 via a working electrode 212 and a counter electrode 222. The bias voltage may be modulated sinusoidally or with any other suitable waveform shape (e.g., a square wave, a triangle wave, a saw tooth, or a more sophisticated waveform shape). For multilayer structures, the bias voltage may be chirped or swept over a particular frequency band (e.g., 0.01 Hz to 1 Hz). The amplitude, frequency, phase, and bias (DC offset) may be selected or adjusted based on the thin-film device 200, the desired measurement, or both. Suitable amplitudes range from tens to hundreds of millivolts of peak-to-peak voltage (e.g., ±86 mV) at DC bias voltages of tens to hundreds of millivolts (e.g., 90 mV). Higher voltages (e.g., tens, hundreds, and thousands of volts) are also possible. Suitable frequency ranges run from 0.0001 Hz to 100 Hz (e.g., 0.001 Hz, 0.01 Hz, 0.1 Hz, 1 Hz, or 10 Hz) with higher frequencies feasible.

In the example shown in FIG. 2A, the thin-film device 200 includes a non-stoichiometric oxide film 210 and an ionically conducting substrate 220 sandwiched between the working electrode 212 and the counter electrode 222. The applied voltage pumps gas, here in the form of oxygen ions, into and out of the non-stoichiometric oxide film 210, causing it to contract and expand. (The applied voltage produces a negligible volume change in the ionically conducting substrate 220.) This expansion and contraction causes the entire thin-film device 200 to change shape (e.g., deflect or change in thickness). The exact change in shape depends on the geometry of the thin-film device 200 and the applied voltage.

A probe 230 touching at least one surface of the thin-film device 200 displaces as the thin-film device 200 changes shape. It produces an electrical signal (e.g., a voltage) that is measured by a lock-in amplifier 240 coupled to an oscilloscope 242. The lock-in amplifier 240 uses the applied voltage from the voltage source 246 to extract the electrical signal from the probe 230 from what may be extremely high background noise. This repeated acquisition of deformation via the sinusoidally varied input stimulus at a fixed oscillation frequency increases the signal-to-noise ratio (SNR) of the detected signal and enables measurement of probe displacement on the order of nanometers.

The lock-in amplifier 240 and oscilloscope 242 may be replaced or augmented by an analog-to-digital converter (ADC), a processor, and a memory. The ADC digitizes the signal from the probe 230, and the processor records the resulting digitized signal in the memory. The processor may process the digitized signal in real-time, postprocessing, or both. For instance, the processor may filter the digitized signal based on the frequency and phase of the voltage applied to the oxide film device, e.g., to enhance one or more spectral components of the digitized signal.

The system 202 also includes an optional heater 244 that heats the thin-film device 200 to a desired temperature. The exact temperature depends on the measurement. For fuel cells and high-temperature actuators, the temperature may be about 450° C. to about 800° C. (e.g., 600° C.); for batteries, the temperature may be room temperature (about 25° C.).

Figure 8:
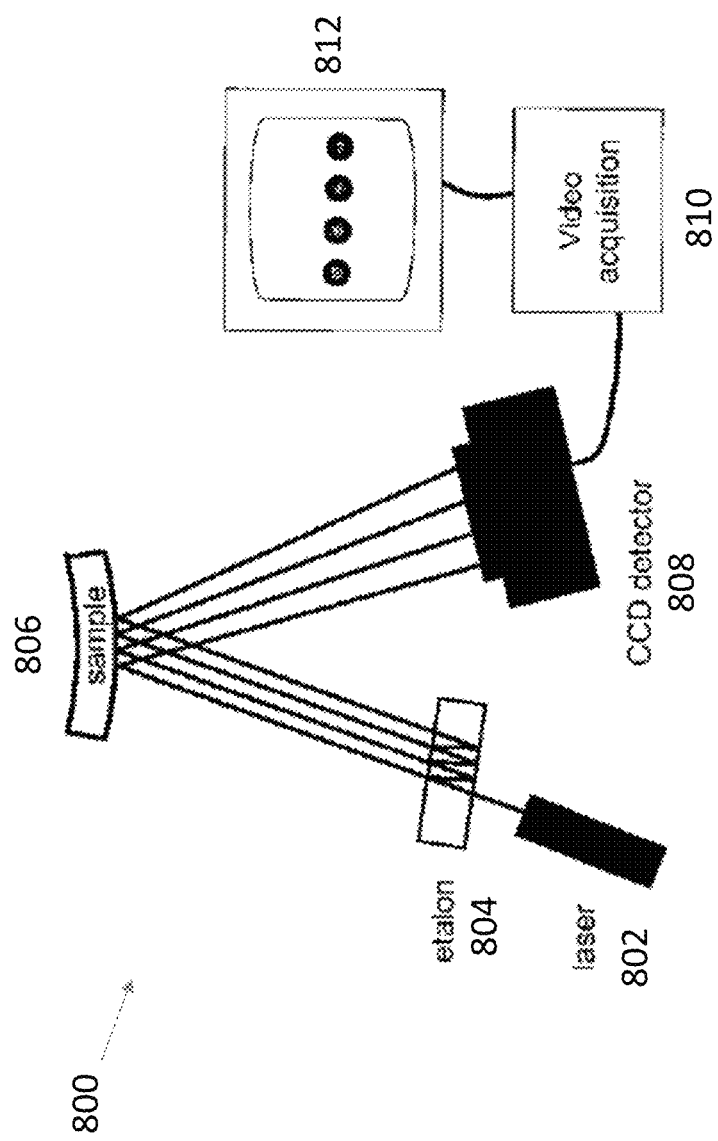
FIG. 8 shows a NECS measurement system using a multi-beam optical stress sensor (MOSS).

The system 202 shown in FIG. 2A can be used or modified to measure displacement using other types of sensors (e.g., optical sensors as shown in FIG. 8 and described below) and in response to other types of time-varying stimuli. For instance, the system 202 may measure deflection or thickness changes in caused by fluctuating device temperature. In this case, the applied voltage may be held constant (or not), and the heater 244 is controlled to alternately heat and cool the thin-film device 200. The modulation signal used to control the heater 244 is also used as a reference by the lock-in amplifier 240 to filter the displacement signal produced by the probe 230. Other types of time-varying stimuli include, but aren't limited to time-varying magnetic fields, pressures, and oxygen partial pressures.

Figure 2B:
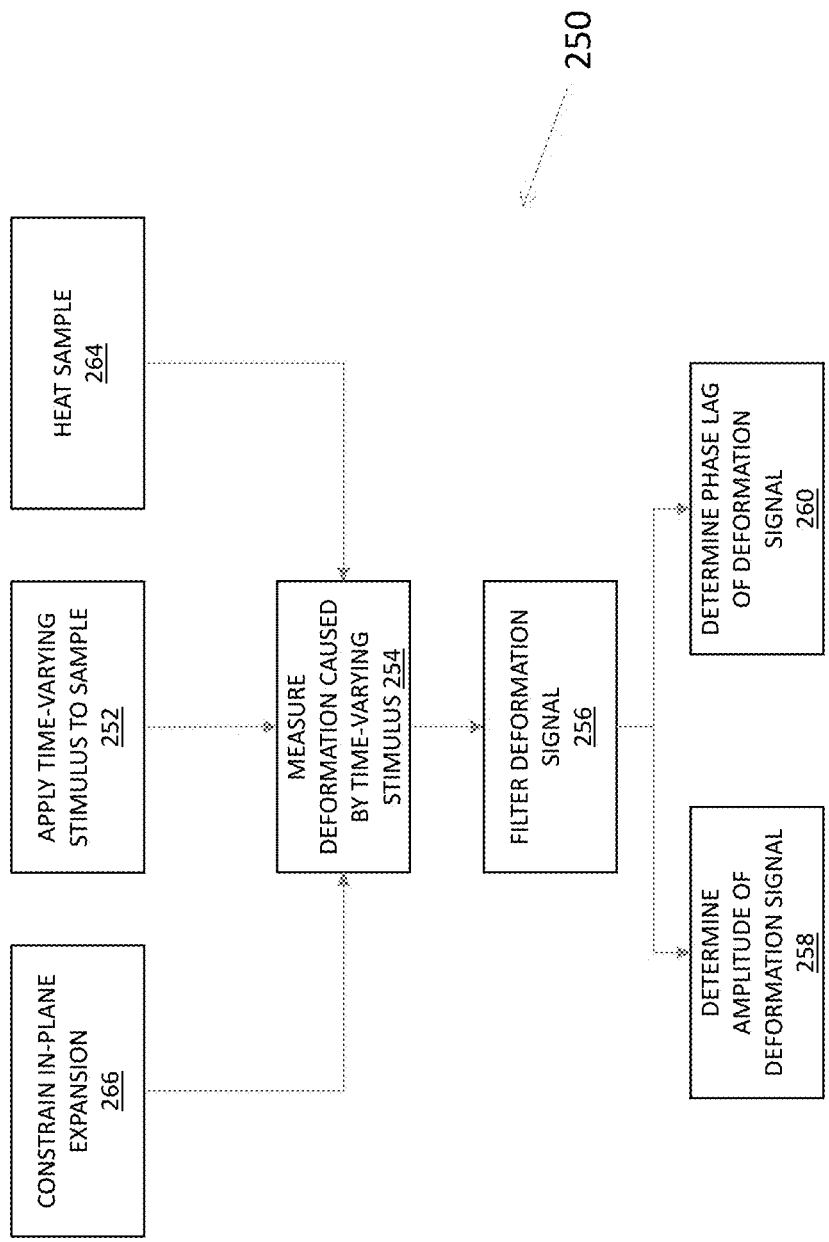
FIG. 2B illustrates a process for performing NECS on a sample that undergoes chemical expansion in response to an applied stimulus (e.g., a bias voltage, heat, pressure, etc.).

FIG. 2B illustrates a process 250 for making NECS measurements. The process 250 includes applying a time-varying stimulus, such as a sinusoidally modulated or chirped voltage varied at a rate of about 0.01 Hz to 1 Hz, to a sample under test, such as thin-film structure that includes an oxide layer (252). The sample may also be heated (264) to a desired temperature (e.g., above 450° C., above 550° C., or above 650° C.). If desired, the sample may be constrained to prevent in-plane expansion during measurement, e.g., via mechanical clamping or special growth techniques.

The time-varying stimulus causes the sample to deform. This deformation may be an out-of-plane chemical expansion or a deflection due to interfacial stress and is measured using a probe or optical sensor to produce a deformation signal (254). This deformation signal may be filtered (256) to increase the SNR. A processor identifies an amplitude (258) and phase lag (260) for each spectral component of the deformation signal. The phase lag is the phase difference between the modulation of the time-varying stimulus and the modulation, at the same frequency, of the deformation signal.

The amplitude and phase lag of the deformation signal provide information about the rate and magnitude of the probe displacement (sample deformation). The amplitude relates to the amount of chemical expansion that happens in response to the applied stimulus. For a non-stoichiometric oxide like PCO, this is related to the chemical capacitance, which is a measure of how much oxygen the non-stoichiometric oxide can store or release under a particular condition. The phase difference comes more from kinetic limitations. For a thin-film structure with a non-stoichiometric oxide on an ionically conducting substrate, the phase lag stems from diffusion in the ionically conducting substrate. However, other systems may have different kinetically limiting processes, like interfacial charge transfer.

The system and process shown in FIG. 2B are not limited to measuring volume changes due to chemical expansion. They can also be used to measure other material volume changes, such as volume changes due to the piezoelectric effect, and other displacements that are combinations of material deformation and structural deflection (e.g., film breathing or film-substrate bending). They can be used on finished or unfinished devices, including thin-film stacks, to determine material characteristics including activation energies of deformation and material compatibility.

Experimental Probe-Based NECS Measurements

FIGS. 3A-3C illustrate probe-based experimental measurements of nanometer-scale displacement and sub-second-scale temporal resolution at temperatures up to 650° C. In these experiments, a film of up to micrometer-scale thickness was electrically biased with modest voltages (e.g., ~100 mV) to drive oxygen content changes within the entire film by adjusting the Nernst electrochemical potential. The film acted as a proxy for a battery, fuel cell, actuator, sensor, or other device that undergoes chemical expansion in response to a change in applied bias voltage. The corresponding strain ε arising from the change in non-stoichiometry Δδ follows the chemical expansion coefficient of PCO (0.087) defined in Equation 7:

$$\varepsilon = \alpha_c \Delta \delta \quad (7)$$

FIG. 3A shows the film configuration and measurement for a sample thin-film device 300 at a constant elevated temperature. The sample 300 included a thin PCO film 310 (e.g., with a thickness of about 300 nm to about 1000 nm) and approximately 8×8 mm in-plane dimensions on a yttria stabilized zirconia (YSZ) single-crystal substrate that was 1 mm thick. The sample 300 had three electrodes: a porous platinum (Pt) current collector 312 on the PCO film 310, a porous Pt counter electrode 322 on the YSZ substrate opposite 320 the Pt current collector 312, and a Pt reference electrode 324 on the YSZ substrate 320. The Pt reference electrode 324 was electrically isolated from the PCO film 310 and the other electrodes 312 and 322.

FIG. 3B illustrates a depth-sensing probe 330 in contact with the PCO sample surface, with the sample 300 maintained at a constant temperature ranging from 550° C. to 650° C. The probe 330 was placed in contact with the film surface as a sinusoidal electrical bias $V_{WE}$ was applied to the working electrode 312 with respect to the reference electrode 324, causing mechanical displacement that the probe 320 detected as a combination of film thickness change and film-substrate structural deflection.

Without being bound to any particular theory, the sinusoidally alternating bias $V_{WE}$ applied to the current collector 312 electrode with respect to the reference electrode 324 modulates the oxygen activity in the PCO film 310, causing oxygen vacancies (empty squares) to be pumped in and out of the PCO film 310 through the YSZ substrate 320. This in turn leads to a mechanical response that is the result of a combination of film volume change and substrate deflection due to PCO chemical expansion, detectable through displacement of the probe 330. More precisely, the PCO film's adherence to the YSZ substrate 320 constrains in-plane chemical strain to produce interfacial stress that can induce detectable deflection.

FIG. 3C is a plot of the applied bias and probe displacement measured as shown in FIG. 3B. The sinusoidal applied bias induces a corresponding and lagging change in probe position, from which phase lag $\phi$ and amplitude A are derived in postprocessing. Positive probe displacement indicates increased film thickness (expansion) and positive substrate curvature and is driven by negative (reducing) bias, whereas negative displacement indicates decreased film thickness (contraction) and negative substrate curvature that is driven by positive (oxidizing) bias. Put differently, the positive applied bias causes negative probe displacement as the film contracts, while a reduction in bias produces concomitant, reversible film expansion and positive probe displacement. This coupling of electrical bias and mechanical displacement at high temperature show that NECS works in extreme operating environments.

The oxide film contraction under positive bias shown in FIG. 3C is expected from the $pO_{2,eff}$ in the film given by Eq. 4. Without being bound to any particular theory, the asymmetry in magnitude of the mechanical response apparent in FIG. 3C is reasonably explained by the asymmetry in defect concentration change with respect to applied bias: PCO tends toward stoichiometry ($\delta \to 0$) under more oxidizing conditions and toward $\delta = 0.05$ for more reducing conditions. This reversible, nanometer-scale mechanical response appeared under electrical biasing frequencies ranging from 1 Hz to 0.01 Hz. Probe displacement on film-free control samples exposed to oscillatory electrical bias was <1 nm, indicating that there was little to no detectable contribution to the measured mechanical response from dimensional changes in the substrate, counter-electrode, or current collector. The curvature of the film/substrate system was detected by acquiring measurements at multiple surface locations with mm-scale lateral spacing relative to the film center. Therefore, the dynamic actuation exemplified in FIG. 3B is likely caused by a concurrent increased PCO film thickness and positive substrate curvature due to interfacial stress.

In the case of PCO, reducing $pO_{2,eff}$ and elevating temperature enhance chemical expansion effects. Other materials may respond differently to identical stimuli. For instance, perovskite $SrTi_{0.65}Fe_{0.35}O_{3-\delta}$ (STF) responds similarly to reducing $pO_{2,eff}$, but shows little (in fact, slightly opposite) dependence on temperature.

Nanoscale Electrochemomechanical Spectroscopy and Complex Admittance

Figure 4B:
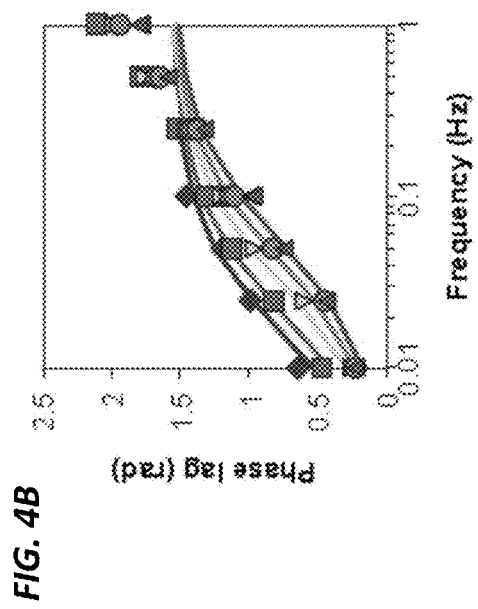
FIG. 4B is a plot of phase lag versus electrical bias modulation frequency at different temperatures for PCO film thickness of 1 micron.
Figure 4A:
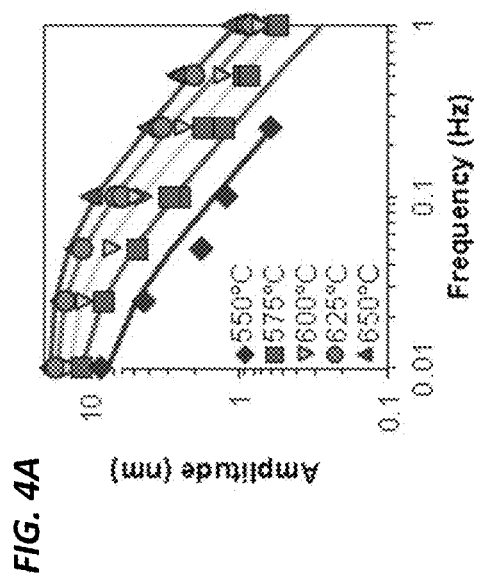
FIG. 4A is a plot of amplitude versus electrical bias modulation frequency at different temperatures for PCO film thickness of 1 micron.

The oscillatory mechanical response shown in FIG. 3C may be characterized by a phase lag $\phi$ and amplitude A by fitting a sinusoidal function to the probe position. Given sufficient time to relax following a change in oxygen activity, the sample can equilibrate fully. Accordingly, with decreasing frequency, the amplitude approaches a maximum value (~10 nm), whereas the phase lag approaches zero as shown in FIGS. 4A and 4B, respectively, for a sample with a 1-micron thick PCO film measured at different temperatures using the setup of FIGS. 3A and 3B. The frequency at which the maximum amplitude is reached increases at higher temperatures with concurrent reduction in oxygen transport barriers.

As mentioned above, this mechanical characterization of the sample frequency response is called nanoscale electrochemomechanical spectroscopy (NECS) in analogy to electrical admittance spectroscopy. In NECS, a complex function Y describes the frequency response of the material relative to the applied signal. In the time domain, Y is the ratio of displacement D to applied bias E described by Eq. 8:

$$Y[t] = \frac{D}{E} = \frac{A[\omega]\sin(\omega t + \varphi[\omega])}{E_0 \sin(\omega t)} \tag{8}$$

Above, $\omega$ is the measurement frequency, and $E_0$ is the applied bias amplitude. This can also be expressed in the complex plane according to Eq. 9:

$$Y[\omega] = \frac{A[\omega]}{E_0}(\cos(\varphi[\omega]) + i\sin(\varphi[\omega])) \tag{9}$$

Figure 5:
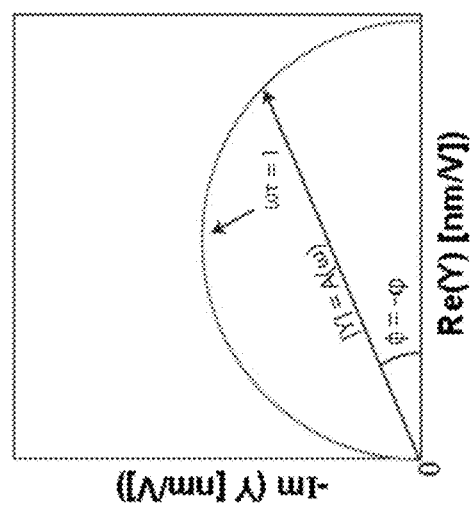
FIG. 5 is a plot of the complex electromechanical admittance for a notional sample.

FIG. 5 shows schematically how this function may be plotted on the complex plane using the frequency-dependent phase lag $\phi[\omega]$ and amplitude $A[\omega]$ defined by Eqs. 10 and 11:

$$A = \frac{D_0}{\sqrt{(\omega\tau)^2 + 1}} \tag{10}$$

$$\phi = -\varphi = \tan^{-1}(\omega\tau) \tag{11}$$

As shown in FIG. 5, plotting the complex frequency response in Cartesian coordinates yields a semicircle terminating at the origin, with the x and y axes representing the real and imaginary parts of Y in nm/V. Each point on the plot can also be represented by its modulus $|Y|=A(\omega)$ (amplitude as a function of frequency) and phase lag $\phi[\omega]$, which is equal to the negative of the phase shift $\varphi$ (also known as the phase angle). The maximum $|Im(Y)|$ in each semicircle indicates the point at which $\omega\tau=1$.

Figure 6:
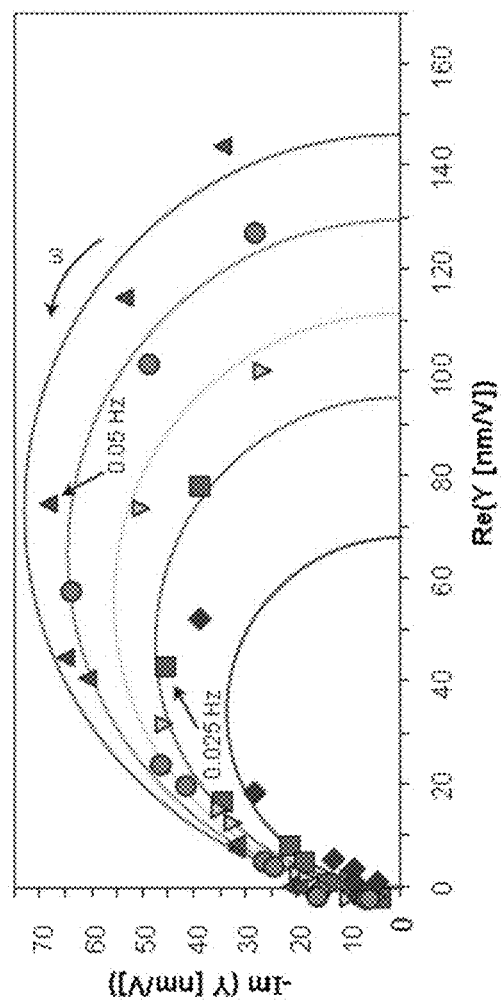
FIG. 6 is a plot of the complex electromechanical admittance for the data of FIGS. 4A and 4B.

FIG. 6 is a plot of the electrochemomechanical admittance Y for the data of FIGS. 4A and 4B. The plot indicates a single semicircle or process at each temperature. In analogy to electrical admittance spectroscopy, corresponding diameters are equivalent to $D_0/E_0$, while the frequency at the semicircle maximum marks $\omega\tau=1$. For all data points, the standard deviation of fitted A or $\phi$ over ten periods is smaller than the data points.

FIGS. 4A and 4B show that the measured deflection amplitudes and phase lags were well described by Eqs. 10 and 11, except at the highest frequencies ($\geq 0.5$ Hz) where phase lag is expected to asymptotically approach $\pi/2$ but exceeds this value experimentally. This discrepancy may be explained by a slight internal signal collection delay. When these data are expressed on the complex plane for a given condition, as in FIG. 6, the displayed NEC spectrum (complex admittance) shows a single characteristic maximum (e.g., ~0.05 Hz at 650° C.) corresponding to the characteristic frequency of the sample (where $\omega\tau=1$). The arc diameter in FIG. 6 corresponds to the maximum mechanical displacement $D_0$, normalized by applied bias amplitude $E_0$, and $\tau/D_0$ is the inverse rate of displacement. Note that the above relationships and following kinetics analysis are valid even for displacement attributed to concurrent film expansion and substrate curvature.

Temperature Effects

The capacity to rapidly measure these breathing displacements over a wide range of temperatures and bias-modulated defect contents enables determination of the activation energies $E_a$ indicative of mechanisms by which oxygen moves in and out of functional oxides. FIGS. 4A and 4B show that for a fixed frequency, PCO generally exhibits increased displacement and decreased phase lag with increased T. In other words, the sample deflection is faster, or activated, at higher temperatures.

Figure 7A:
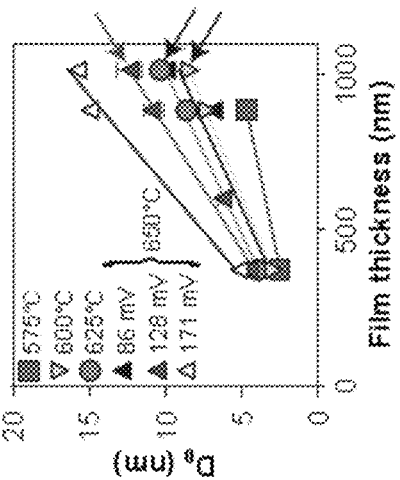
FIG. 7A shows representative Arrhenius plots used to estimate the activation energy for YSZ diffusion and PCO chemical capacitance based on the values of $\tau/D_0$ (inverse deflection rate) and $D_0$ (deflection magnitude), respectively, identified from the mechanical measurements.

FIG. 7A shows representative Arrhenius relations from which the activation energies modulating the magnitude of mechanical response $D_0$ and inverse rate of expansion $\tau/D_0$ for a given sample and condition were determined. These average $E_a$ values were $-1.05\pm0.13$ eV (for $\tau/D_0$), and $0.53\pm0.14$ eV (for $D_0$), reported as mean and standard deviation of at least 6 measurements across 3 samples. The data shown are for PCO film thickness $371\pm11$ nm.

Conventional in situ impedance spectroscopy (IS) applied to the same sample constructs at 500° C. to 700° C. allowed for separate measurements of $E_a$ associated with electrical impedance between different working electrodes. They showed that the distinct activation energies measured mechanically were consistent with those attributable specifically to the oxygen storage capacity, i.e., chemical capacitance, of the PCO film ($E_a$ measured by IS at $0.55\pm0.07$ eV corresponds to displacement magnitude $D_0$) and to resistance to oxide ion conduction through the YSZ ($E_a$ measured by IS at $-0.99\pm0.06$ eV corresponds to inverse displacement rate $\tau/D_0$). These activation energies also agreed well with those reported previously for PCO chemical capacitance (0.6 eV) and YSZ diffusion (1 eV). In the high $pO_2$ regime investigated here, chemical capacitance in PCO exhibits an activation energy that should correlate with the enthalpy of reaction from Eq. 1 and 2, shifted by a factor that is dependent on the average oxygen vacancy content $\delta$. In accordance with the derivations given for $D_0$ and $\tau/D_0$, the good agreement with expected activation energies validated that the calculated maximum breathing displacements $D_0$ of these oxide films are controlled by the chemical capacitance of the thin film PCO, and that the inverse displacement rate $\tau/D_0$ is controlled by the rate of oxygen transport into and out of the PCO film through the YSZ substrate.

FIGS. 7A-7D illustrate factors controlling oxide film breathing. FIG. 7A shows representative Arrhenius plots used to estimate the activation energy for YSZ diffusion and PCO chemical capacitance based on the values of $\tau/D_0$ (inverse deflection rate) and $D_0$ (deflection magnitude), respectively, identified from the mechanical measurements. These activation energies are comparable to those calculated based on in situ impedance spectroscopy. Data shown are for PCO film thickness $371\pm11$ nm.

Figure 7C:
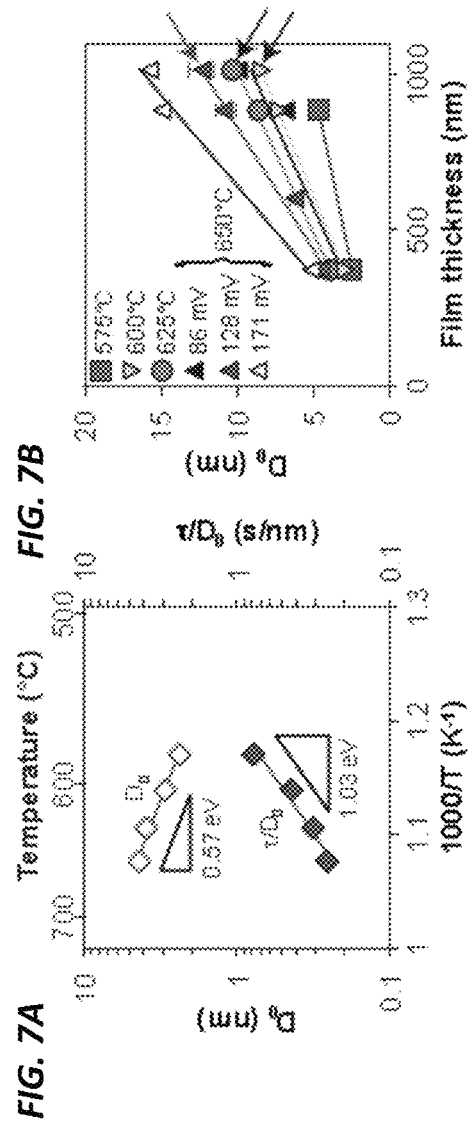
FIG. 7C is a plot of out-of-plane chemical strain $\epsilon$ and non-stoichiometry change $\Delta\delta$ vs. applied bias at several temperatures for a constrained PCO thin film as predicted by the defect model for PCO.
Figure 7B:
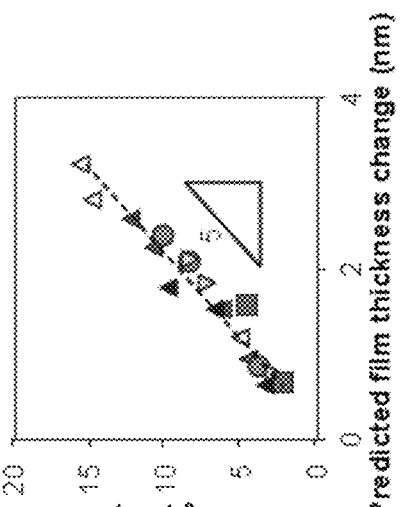
FIG. 7B is a plot of the equilibrium magnitude $D_0$ versus film thickness for different values of applied bias voltage and sample temperature

FIG. 7B is a plot of the equilibrium magnitude $D_0$ of probe displacement versus film thickness for films at different temperatures and applied bias amplitudes $E_0$. Data correspond to $E_0$ of 128 mV unless otherwise noted. Where possible, error bars show the range of measured $D_0$ values for three replicate measurements (All films are at $E_0=128$ mV and T=650° C., indicated by the upper arrow, and all temperatures with $E_0=128$ mV for the film with thickness $1018\pm26$ nm, indicated by the lower pair of arrows). This range is often smaller than the size of the data points.

FIG. 7B shows that $D_0$ was approximately linear with film thickness $t_f$, for different temperatures and applied bias amplitudes, with a vertical intercept at $t_f=0$ of $D_0\sim\pm1$ nm similar to that detected for control samples (i.e., YSZ substrates with no PCO film). The displacement amplitude increased with increasing temperature at a given applied bias, e.g., up to 12 nm at 128 mV and 650° C. for the 1018 nm film. Further, increasing the amplitude of the applied bias from 128 mV to 171 mV (increasing $pO_{2,eff}$ range by two orders of magnitude) at a constant temperature of 650° C. increased $D_0$ of that sample to 16 nm. The observed mechanical response to rapid changes in electrical bias indicates dimensional oscillation in the PCO film that is driven by corresponding changes in oxide ion vacancy content.

FIG. 7C is a plot of out-of-plane strain E and non-stoichiometry change $\Delta\delta$ vs. applied bias at several temperatures for a constrained PCO thin film as predicted by the defect model for $Pr_{0.1}Ce_{0.9}O_{2-\delta}$.

Figure 7D:
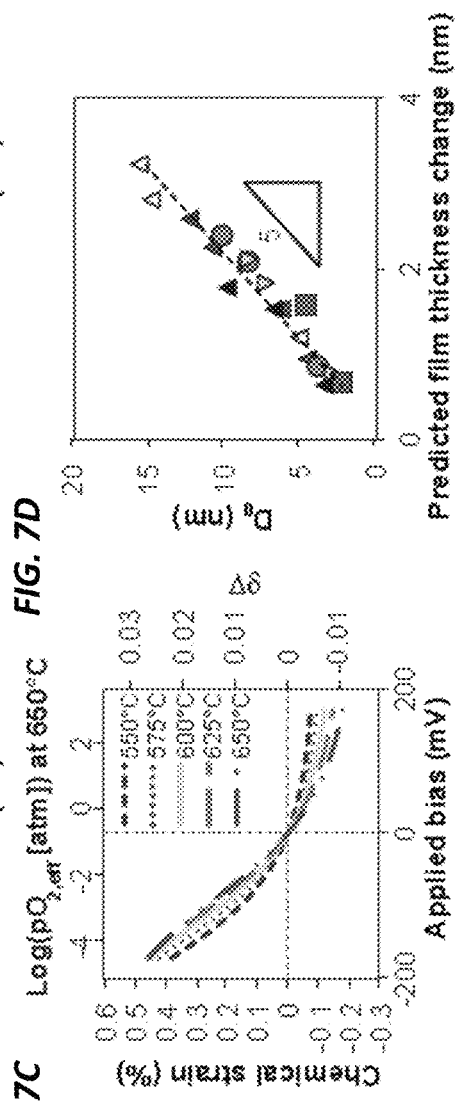
FIG. 7D is a plot of measured deflection amplitude $D_0$ vs. predicted film thickness change based on chemical strains plotted in FIG. 7C for the set of measurements shown in FIG. 7B.

FIG. 7D shows measured deflection amplitude $D_0$ vs. predicted film thickness change based on chemical strains calculated in FIG. 7C for the set of measurements shown in FIG. 7B. A consistent amplification of $5\pm0.5$ nm/nm ($\Delta D_0/\Delta\varepsilon$) is observed across all samples, temperatures, and $E_0$ values, with error determined by bootstrapping.

Calibration, Electrode Material, and Oxygen Pumping Effects

For more precise results, it can be helpful to calibrate the substrate deflection/displacement signal amplification factor used by the NECS system to the sample geometry before acquiring deflection-based measurements of quantitative chemical expansion (film strain as a function of applied bias). PCO is an excellent model material for calibration because there are accurate chemical expansion models for this material. For the geometry and attachment method of samples observed in FIGS. 3A-3C (1 mm substrate thickness, $0.8\times0.8$ cm$^2$ film area) substrate deflection amplified the displacement signal by a factor of 5 relative to film thickness change alone, as highlighted in FIG. 7D.

In addition, the choice of electrode metal applied to the sample may limit the temperature range for NECS measurements. For example, the use of silver paste to attach Pt wire to Pt electrodes sets the maximum temperature in FIGS. 3A-3C to about 650° C. An alternative choice could raise that temperature.

Additionally, samples that have very fast surface oxygen exchange may experience oxygen leakage competing with electrochemical pumping; suggestions for mitigating this include use of blocking electrodes and designing samples where oxygen pumping is fast enough to overcome this limitation (e.g., by thinning the oxide ion conducting substrate).

Derivations for Nanoscale Electrochemomechanical Spectroscopy (NECS)

An analysis of chemical expansion in PCO films based on nanoscale dynamic measurements of amplitude A and phase lag $\phi$ of sample displacement during electrochemical stimulation appears above. These parameters are presented both as measured (FIGS. 4A and 4B) and in the complex plane (FIG. 6), and are related to a complex function Y known as the electrochemomechanical admittance, which has units of nm/V and is defined according to Equation 12 in the time domain, and Equation 13 in the frequency domain:

$$Y[\omega] = \frac{A[\omega]}{E_0}(\cos(\varphi[\omega]) + i\sin(\varphi[\omega])) \qquad (12)$$

-continued $$Y[t] = \frac{D}{E} = \frac{A[\omega]\sin(\omega t + \varphi[\omega])}{E_0 \sin(\omega t)} \quad (13)$$

In the above equations, D is displacement, E is electrical bias (which has amplitude $E_0$), and ω is frequency. Although |Y| is generally normalized by $E_0$ (constant for all frequencies in a given condition), this bias normalization factor can be omitted when comparing datasets under constant bias amplitude to indicate the measured mechanical response in units of nm, as in the Bode plots of FIGS. 4A and 4B.

This model describes the measured φ and A of the mechanical response of the films according to fundamental processes within the material. The components of Y may be modeled using an equivalent circuit with a real component, conductance G, and an imaginary component, susceptance B, in series. The admittance of these two components is denoted $G\tilde{O}$ and $1/i\omega B\tilde{O}$, respectively, giving rise to a total admittance described by Eq. 14:

$$\tilde{Y} = \left(\frac{1}{G} + \frac{1}{B}\right)^{-1} = \frac{G'}{1 + (\omega G'B')^2} - \frac{G' i\omega G'B'}{1 + (\omega G'B')^2} \quad (14)$$

In this representation, $\tilde{Y}=G\tilde{O}$ when ω=0 (equilibrium), and G'B' represents a characteristic time constant τ for the response. Therefore, $G'=D_0/E_0$ and $G'B'=\tau$, where $D_0$ is the equilibrium expansion amplitude for $E_0$ (a constant across all frequencies), and values for τ are determined as described above. These substitutions yield Eq. 15:

$$\tilde{Y} = \frac{D_0/E_0}{1 + (\omega\tau)^2} - \frac{(D_0/E_0 i\omega\tau)}{1 + (\omega\tau)^2} \quad (15)$$

As shown in FIGS. 4A and 4B, it is common to provide the modulus of admittance and phase angle on a Bode plot. The modulus is given by the root of the sum of the squared real and imaginary parts of Y, and the phase angle is equal to the inverse tangent of the ratio of the imaginary and real components as described in the following equations:

$$|Y| = \left(\left(\frac{D_0/E_0}{1 + (\omega\tau)^2}\right)^2 + \left(\frac{(D_0/E_0 \omega\tau)}{1 + (\omega\tau)^2}\right)^2\right)^{1/2} = \frac{D_0/E_0}{\sqrt{1 + (\omega\tau)^2}} \quad (16)$$

$$\varphi(\omega) = \tan^{-1}\left[-\frac{D_0/E_0 \omega\tau}{D_0/E_0}\right] = \tan^{-1}[-\omega\tau] \quad (17)$$

Multiplying Eq. 16 by the constant applied voltage amplitude $E_0$ results given above, and rearranging Eq. 17 results in Eq. 19:

$$A(\omega) = \frac{D_0}{\sqrt{(\omega\tau)^2 + 1}} \quad (18)$$

$$\varphi(\omega) = -\phi = \tan^{-1}(-\omega\tau) \quad (19)$$

$A(\omega)/E_0$ and $\phi(\omega)$ are the modulus and phase angle, respectively, of Eq. 12, confirming that Eq. 14 is an equivalent representation of Y. These are shown schematically in FIG. 5.

With the above equations, $D_0$ and τ can be derived based on the mechanical measurement of A and φ and related to the fundamental processes contributing to the measured electromechanical admittance.

Note that as equilibrium is approached (ω→0), the admittance is entirely real and equivalent to $G\tilde{O}=D_0/E_0$. This value yields information about the total possible mechanical response, and is proportional to the charge storage capacity of the PCO film, given by the chemical capacitance ($C_{chem}$), as shown by the following proportionality relation:

$$\frac{D_0}{E_0} \propto \frac{\alpha_c \Delta \delta}{E_0} \propto \frac{\Delta q_\delta}{E_0} \propto C_{chem} \quad (20)$$

where $D_0$ is proportional to $\alpha_c \Delta \delta$, the chemical expansion, which, in turn, is proportional to the change in number of charges stored as oxygen vacancies, $\Delta q_\delta$, with $C_{chem}$ being the ratio of stored charge for the given applied voltage.

This correlation is validated by the fact that charge accumulation in the film determined from I-V data during experiments tracked displacement data with the same phase lag relative to the applied voltage sinusoids. In FIG. 6, this quantity is also equivalent to the diameter of the semicircle. Since $E_0$ is a constant (128 mV), an Arrhenius fit, such as the fit shown in FIG. 7A, to the equilibrium expansion amplitude $D_0$ gives an activation energy corresponding to that of chemical capacitance in this PCO film. The value measured is 0.53±0.14 eV (standard deviation of 6 measured activation energies), which agrees well with previously reported values for chemical capacitance in PCO and the values reported in this study measured by impedance spectroscopy on these same samples.

Turning to B', when the response of the system is completely out of phase (φ=−π/2) to the applied signal, the complex admittance is entirely imaginary and equivalent to B=1/iωB', where $B'=\tau/G'=\tau E_0/D_0$. As described above, τ is a time constant describing the rate of a process and, following an equivalent circuit representation, can be recast as a resistance multiplied by a capacitance (i.e., RC time constant). As $E_0/D_0$ is the inverse of $C_{chem}$, B', from this approach, is equal to a resistance, R (i.e. the resistance to charge passage into the PCO thin film). As described next, this resistance is equivalent to the resistance for ionic transport through the YSZ electrolyte.

As shown schematically in FIG. 3B, during the experiments outline above the electrical bias $V_{WE}$ was applied between the PCO/Pt working electrode 312 and the reference electrode 324 on the YSZ substrate 320. Since resistance to oxygen gas exchange at the PCO/Pt electrode 312 is much higher than that of oxygen transport through the YSZ (>100 Ωcm² vs. 10 Ωcm², respectively at 650° C.), as the PCO film 320 adjusted its vacancy content to match the $pO_{2,eff}$ caused by $V_{WE}$, oxygen was pumped primarily through the YSZ electrolyte. The rate of adjusting oxygen content in the PCO film was then limited by diffusion through the YSZ, which in turn determined the expansion rate. This interpretation is further validated by comparing the activation energy for $\tau/D_0$ (1.05±0.13 eV) with the activation energy for ionic conduction in YSZ (~1 eV).

Optical, Non-Contact NECS

NECS can also be used with optical, non-contact displacement sensors to measure chemical expansion in oxide thin films, including in fuel cells, batteries, actuators, sensors, and other thin film devices. Here, the analysis outlined above is used to infer characteristic parameters, such as amplitude and phase lag of deformation, but different devices are employed to quantify deformation. Optical sensors can be used at standoff distances, making them suitable for measurements in hot, harsh environments. For example, they can be used for measuring changes in the Li storage material (e.g., $Li_{1-x}Mn_2O_4$) used in Li-ion batteries (LIBs) as explained below.

LIBs are generally operated at ambient temperatures and are repeatedly cycled through their full range of reversible Li-storage capacity such that the Li density also varies temporally and spatially operando. In contrast, solid oxide fuel cells (SOFCs) are operated at temperatures in excess of 500° C. and exhibit steady-state composition gradients due to the range of oxygen partial pressures experienced on either side of the electrolyte operando. Although there may be local fluctuations in composition and electrochemical potential within SOFC electrodes and electrolytes during normal operation, larger-scale, more persistent changes in these values would only occur in more unusual applications or circumstances, such as redox cycling or fuel interruption. Therefore, rate dependence and cyclability are of particular interest in understanding electrochemomechanical coupling in Li-storage compounds, as these materials regularly and continuously undergo changes in composition and therefore associated composition-dependent properties during normal operation.

The conventional method for detecting structural changes of ionic conductors in situ, X-ray diffraction, has limited temporal resolution without access to a synchrotron. Because the operando conditions for Li-ion batteries tend to be far from equilibrium, it is of interest to demonstrate the ability to detect chemical expansion in Li-storage materials operando in order to elucidate any useful information about rate-dependent chemical expansion. Such techniques could also be used to characterize solid-state actuator devices based on room temperature intercalation compounds like LMO. Fortunately, the NECS principles outlined above can be used in a non-contact, optical approach to study chemical expansion in LMO, drawing from the same principles of dynamic chemical expansion detection outlined above.

FIG. 8 shows a multi-beam optical stress sensor (MOSS) 800 suitable for making NECS measurements. It can be used in addition to or instead of the probe 230 in the system 202 of FIG. 2A. The MOSS 800 includes a laser 802 that shines a beam of light on an etalon 804 at an angle. The etalon's front and back surfaces are partially reflective, so they transmit and reflect portions of the beam to produce an array of parallel laser beams that illuminate a surface of a sample 806. The beams reflect off the sample 806 to illuminate a detector array 808, such as a charge-coupled device (CCD), which produces an electrical signal with peaks corresponding to the beam positions on the detector array 808. The detector array 808 may be one-dimensional or two-dimensional depending on the expected nature of the sample deformation.

Applying a time-vary stimulus, such as an alternating bias voltage, to the sample 806 causes the sample 806 to deform. This deformation causes the sample to reflect the incident beams in different (i.e., non-parallel) directions. For example, if the sample 806 bulges outward as shown in FIG. 8, the beams may diverge. The detector array 808 detects this divergence as shifts in the beam positions that produce corresponding shifts in the positions of the peaks in the detector array's output.

Experimental Measurements of LMO Deformation with Optical NECS $Li_yMn_2O_4$ (LMO) is another material that can be measured using NECS. This spinel oxide is a low cost, environmentally benign Li-intercalation material with a large initial energy storage capacity. This Li intercalation causes a volume change that results in material deformation. LMO is typically cycled in the range 0<y<1 because of severe capacity fade that occurs for y>1. The crystal structure of LMO is within the Fd3m space group, with Li located at 8a tetrahedral sites and Mn at 16d octahedral sites within the oxygen (32e) sublattice. While the stoichiometric structure (y=1) is cubic, Jahn-Teller distortions and orthorhombic crystal distortion have been observed for off-stoichiometric Li compositions and at low temperatures. Several experimental and computational studies have characterized the phase diagram of LMO, and together can be summarized by the statement that delithiation decreases material volume for y<1, and increases material volume for y>1. Therefore, for a film of LMO of y<1 adhered to a substrate of significantly higher stiffness (effectively rigid), delithiation should increase tensile stress within the film due to contraction under the film-substrate constraint.

A typical charge-discharge hysteresis for LMO proceeds between 3.5 and 4.3 V and exhibits two plateaus in the voltage profile at ~4.05 and 4.16 V, indicative of phase changes initiated at these electrical potentials. The exact positions of these plateaus depend on the oxygen non-stoichiometry. The focus here is on the effects of charge and discharge rate on the stress development within LMO films. In contrast to a PCO solid film adhered to a YSZ substrate that served as a solid electrolyte, the LMO film under consideration here is adhered to a substrate that does not participate in charge storage or transfer, and the electrolyte is a liquid. Therefore, the rate of chemical expansion of LMO is not controlled by diffusion through a supporting substrate.

LMO Sample Fabrication and Measurement

The measured LMO samples were prepared with solution-deposited LMO films (80-100 nm thickness) and spin-coated Pt electrodes on quartz substrates. A sinusoidal electrical bias was applied to the films using a Biologic VMP3 potentiostat at seven frequencies ranging from $10^{-4}$ to $10^{-1}$ for 10-15 cycles at each frequency. A set of frequencies with an amplitude of 0.3 V was applied for three different mean applied biases (3.8 V, 3.9 V, and 4.0 V) to explore the effect of the applied voltage window on the stress-thickness response of the film. Beaker cells were constructed with a Li foil anode and non-aqueous liquid electrolyte of 1M $LiPF_6$.

Operando stress-evolution measurements were acquired by measuring changes in the curvature of the elastic substrate during electrochemical cycling with the system like the one shown FIG. 8. An array of parallel laser beams incident on the back of the quartz substrate were reflected toward a CCD camera, which recorded changes in spacing between adjacent beams. This spacing d was related directly to substrate curvature κ by Equation 21:

$$\kappa = \frac{d - d_0}{d_0 A_m} \quad (21)$$

where $d_0$ is the initial distance between adjacent beams, $A_m$ is the mirror constant that is dependent on three parameters: the optical path length of the laser from the reflective substrate to the CCD camera, the refractive index of the electrolyte through which the laser travels, and the incident angle of the laser upon the substrate. Changes in curvature were then directly related to the product of stress and film thickness $\langle\sigma\rangle h_f$ using Stoney's formula (Eq. 22):

$$\langle\sigma\rangle h_f = \frac{M_s h_s^2 \kappa}{6} \quad (22)$$

where $\langle\sigma\rangle$ is the thickness-averaged stress in the film, $h_f$ is the film thickness, $M_s$ is the biaxial elastic modulus of the substrate, $h_s$ is the substrate thickness, and K is the curvature of the film-substrate system. Stress measurements were made relative to the initial curvature of the substrate, which was non-zero indicating the presence of some residual stress in the as-prepared films.

LMO Data Analysis

The phase lag and amplitude of detected stress-thickness response data were determined according to the same procedure described above, with some modification for phase lag determination. For this study, two different computers were used to acquire the current-voltage (I-V) data and the $\langle\sigma\rangle h_f$) data, with an unknown time delay between the start of data collection on each computer. This time delay $\tau_d$ was on the scale of ~2 seconds, and arose from the need to initiate data collection on the $\langle\sigma\rangle h_f$ computer as soon as possible after starting the experiment on the I-V computer. This effect is negligible unless determining phase lag for frequencies with a period length on the order of $<10\tau_d$ (e.g., 0.1 Hz and 0.05 Hz). To account for the error in estimated phase lag introduced by this time offset, the fitting form applied to the phase lag vs. frequency data to determine the time constant $\tau$ was modified to include an additional fitting parameter $\tau_d$ according to Eq. 23:

$$\Phi = \tan^{-1}\omega\tau + \tan^{-1}\omega\tau_d \quad (23)$$

In addition to considering the magnitudes of equilibrium displacement amplitude $D_0$ and $\tau$ for the different applied bias ranges, Lissajous plots for these data were produced to allow comparison of the asymmetry of the $\langle\sigma\rangle h_f$ signals in these different ranges, as well as any other interesting rate-dependent features. This type of plot displays the $\langle\sigma\rangle h_f$ output vs. the input voltage averaged over all cycles at each frequency. In general, if the output and input overlapped with no phase lag, then the Lissajous plot appears linear and the slope is related to the amplitude ratio of the two signals. If there was a phase lag, the Lissajous plot appears as a loop around an internal area that increases with increased phase lag. Asymmetry in the output with respect to the input (e.g., differences in positive and negative amplitude) is apparent in the shape of the Lissajous plot as well. Lissajous plots were acquired using a custom Matlab code.

LMO Measurements

Figure 9C:
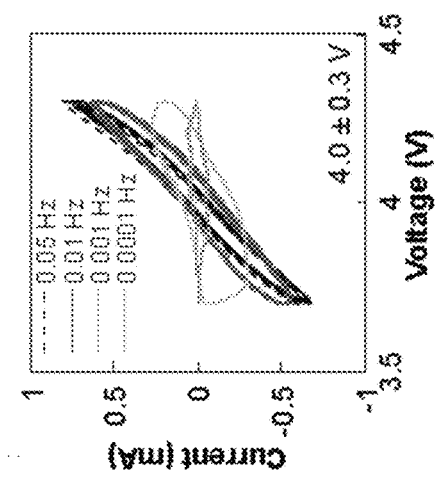
FIG. 9C is a plot of current versus applied bias voltage for a dynamic MOSS measurement of LMO.
Figure 9B:
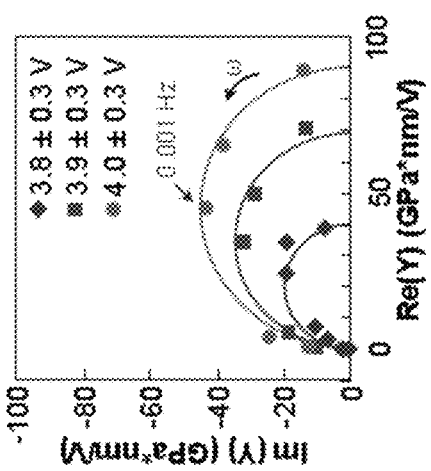
FIG. 9B is a plot of electrochemical admittance spectra for a dynamic MOSS measurement of LMO.
Figure 9A:
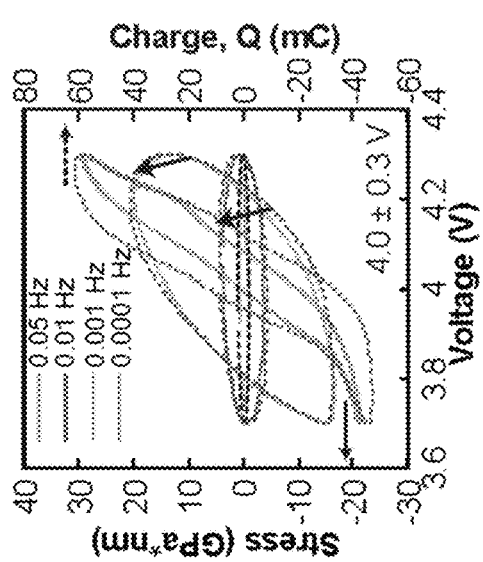
FIG. 9A is a Lissajous plot of stress amplitude and charge versus applied bias voltage for four different bias voltage frequencies applied to a $Li_xIn_2O_4$ (LMO) sample.

FIG. 9A shows Lissajous plots for stress-thickness and charge vs. voltage for an LMO sample at four different frequencies. The charge Q as a function of time t is determined by integrating the oscillatory current I(t) to determine cumulative Q(t). Q(t) is then flattened by subtracting a moving average from the data resulting in data centered at zero charge in FIG. 9A. This should be interpreted as "charge relative to the average at 4 V" in FIG. 9A. Additionally, this procedure effectively removed the contribution of leakage current to the reported data. However, such leakage is present and worth studying over repeated cycling.

First turning to the stress results, ranging the frequency v over four orders of magnitude of frequency produced a variation in the measured stress thickness S spanning over one order of magnitude. This comparison of magnitudes of effect highlights the sensitivity of the MOSS approach, even for a film as thin as 80-100 nm. The plot shows the onset of asymmetry at the lowest frequency ($10^{-4}$ Hz) that is absent for the other tests. In fact, at the slowest frequency features (highlighted by upward pointing arrows) appear in the Lissajous plots that relate to the phase-change plateaus for LMO mentioned above. For faster charging, the magnitude of stress-thickness decreases, as well as the degree of asymmetry, at the cost of decreased accessible capacity.

Turning now to the Q(V) Lissajous plots (dashed lines), these trends were clearly reproduced. While Q(V) and S(V) overlapped almost completely when $v \geq 10^{-3}$ Hz, this overlap disappeared at the slowest frequency. Instead, a phase lag arose along with the asymmetry in the data. This suggests that the detected stress thickness values were not necessarily directly correlated with charge storage, or, in other words, that the chemical expansion coefficient was non-uniform in this sample. This result reflects the ways in which this measurement approach is complementary to standard electrochemical techniques. This approach makes it possible to decouple electrochemical and mechanical effects, using the frequency domain to probe the material at different depths or compositions.

FIGS. 9B and 9C show the electrochemomechanical admittance spectra and current Lissajous plots, respectively, at 4.0±0.3 V obtained for LMO. Like STF and PCO, the spectra are individual semi-circles. However, the mechanism controlling charge transport and the rate of mechanical response is quite different for LMO, as charge moves through a liquid electrolyte that provides no mechanical constraints for sample deflection.

The time constants of these measurements were on the order of ~100 seconds, indicative of the much slower charging rate for LMO at room temperature as compared to STF and PCO at high temperature. For the three voltage ranges investigated, the mechanical response rate (ratio of amplitude to time constant) increased with increased average mean voltage, suggesting that charge transport was faster in the higher mean voltage regimes. Like for PCO and STF, shifting the mean applied bias also changed both the shape and amplitude of the mechanical deflection profile, in this case because the mean Li content shifted as a result.

In general, phase changes can be expected to produce asymmetry in the cyclic profiles at slow frequencies. Comparing the I(V) plots in FIG. 9C to the S(V) and Q(V) plots in FIG. 9A shows that features correlated with redox processes of Li insertion/extraction (inflection points in S(V) and Q(V)), maxima or minima in I(V)) do not necessarily occur at the same voltages. This may be related to the kinetics of the insertion and extraction process, and how these translate to mechanical effects. For example, if a phase has a relatively low nucleation energy barrier, it should grow via a phase change front that propagates uniformly across the film. However, if nucleation and growth kinetics favor multiple small domains nucleating and then growing, a different set of mechanical compatibility conditions will be active. The rate-dependent stress signal provides complimentary information based on a different signal-generation mechanism than electrochemical results, potentially providing an additional way to probe phase change kinetics in Li-storage materials.

Sensitivity Analysis for Direct Measurement of Chemical Expansion

This section discloses an analysis of detection sensitivity and parameter estimation error for the NECS measurements ("direct measurements of chemical expansion") described above. It addresses the measurement error for individual data points collected for phase lag and amplitude, as well as estimation error for parameters $D_0$ and $\tau$ determined based on fits to measurements across the frequency spectrum of interest. The error in activation energies obtained from measurements conducted at multiple temperatures for the same sample is also assessed.

Figures 10A, 10B:
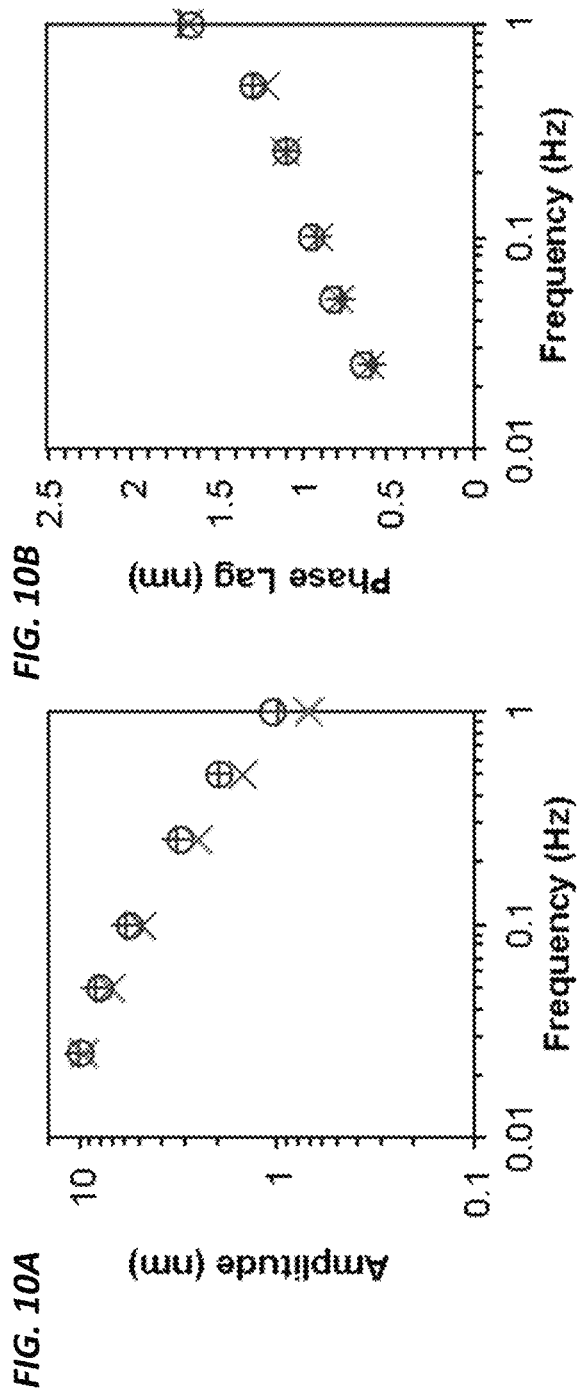
FIGS. 10A and 10B are plots of the amplitude and phase, respectively, versus applied bias voltage frequency for three replicate experiments.

At each experimental condition, oscillatory loading (with real-time analysis) was performed until the phase lag $\phi$ converged to within 0.1 radians and the amplitude A to within 0.5 nm, typically >30 cycles. The values of A and $\phi$ vs. frequency $\omega$ shown in FIGS. 10A and 10B are the averages of the fitted amplitude and phase lag of the last ten cycles of each measurement, which generally had standard deviations of less than 0.3 nm and 0.1 radians, respectively. In FIGS. 10A and 10B, these standard deviations are smaller than the data points. For the slowest frequency measurements (corresponding to the largest measured amplitudes, phase lags nearest to 0, and the most opportunity for mechanical noise and signal drift to affect signal-to-noise ratio), these standard deviations were occasionally larger (<1 nm or 0.2 rad). For replicate measurements performed in the same conditions (temperature, film thickness, applied bias range, etc.) near the centers of the samples, the range of fitted values for $D_0$ was generally ±3-8%, and for $\tau$ was ±2-6%.

Figure 11:
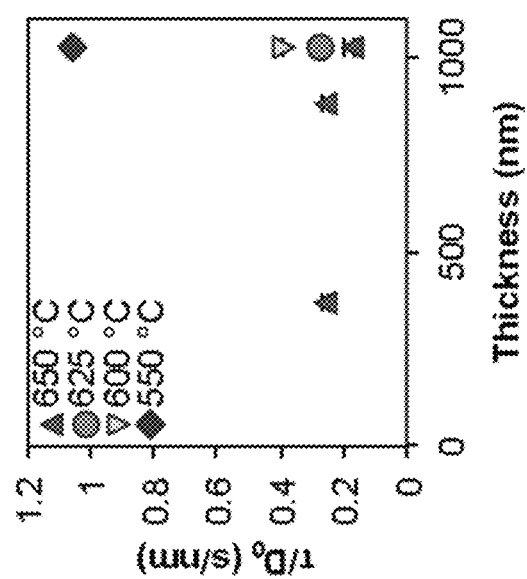
FIG. 11 is a plot of error in the measured inverse deflection rate versus film thickness for replicate measurements at different temperatures.

FIG. 11 shows the result of one of these experiments (650° C., 883 nm film thickness) for the same condition tested at three locations near the sample center. Data points overlapped significantly until the highest frequency when some small deviation occurred in the amplitude data. At this point, the amplitude was ~1 nm, which is the stated lower limit of displacement detection. This set of measurements reflected a worst-case scenario in terms of sampling repeatability, and the actual deviations in the resultant calculated magnitudes of $\tau$ and $D_0$ from this set of measurements was only 6% and 8%, respectively. Calculated $D_0$ and $\tau$ values are therefore robust to experimental variability, and the error of any reported values can be estimated to be within the ranges reported above.

In fact, the parameters used to fit activation energies were $D_0$ and $\tau/D_0$. The sample with film thickness 1028 nm was the only one for which multiple positions near the sample center were tested at multiple temperatures, but for those three tests the activation energies of $D_0$ and $\tau/D_0$ were found to vary by less than 8% and 6%, respectively, displaying minimal sensitivity to experimental variation. FIG. 11 shows the variation in $\tau/D_0$ that was observed when assessment was possible.

The error in measured inverse deflection rate ($\tau/D_0$) vs. film thickness was small whenever replicate measurements were conducted. Error bars denote the range (maximum and minimum) values for each condition.

The sample-to-sample variability can be derived from variation in the quantities that were derived based on data from all samples: activation energies and amplification factor. The average and standard deviation for a total of at least six measured activation energies across three samples are: $-1.05\pm0.13$ eV (for $\tau/D_0$), and $0.53\pm0.14$ eV (for $D_0$). Thus, the sensitivity of the activation energy to experimental and sample-to-sample deviations was on the order of 0.1 eV. Variability in the amplification factor (the slope shown in FIG. 7D that compares measured displacement $D_0$ to predicted film thickness change) can be determined by applying a bootstrapping process (resampling with replacement) to assess the variation in the linear fit for 1000 bootstrapped samples.

This assessment yields 95% confidence intervals for the amplification factor and goodness-of-fit parameter $R^2$ as (4.4, 5.5 nm/nm), and (0.83, 0.98), respectively. Therefore, the sensitivity of the detected amplification factor to sources of variation including but not limited to film thickness measurement error, probe centering error, and sample clamping differences, was on the order of 10%. The amplification factor is related to the specific substrate thickness (1 mm) and film area (0.64 cm$^2$) used throughout this work. A different sample geometry may produce a different amplification factor.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of designing and making the technology disclosed herein may be implemented using hardware, software or a combination thereof. When implemented in software, the software code can be executed on any suitable processor or collection of processors, whether provided in a single computer or distributed among multiple computers.

The various methods or processes (e.g., of designing and making the technology disclosed above) outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of and" consisting essentially of shall be closed or semi-closed transitional phrases, respectively, as set forth in the United States Patent Office Manual of Patent Examining Procedures, Section 2111.03.

The invention claimed is:

1. A method of characterizing a device, the method comprising:
applying a time-varying stimulus to the device, the time-varying stimulus causing a time-varying change in gas content of the device, the time-varying stimulus including an alternating bias voltage; and
measuring, with a probe in contact with a surface of the device, a time-varying deformation of the device caused by the time-varying change in gas content of the device, the time-varying deformation based on chemical expansion or a deflection of the surface of the device induced by the time-varying change in gas content of the device, the measuring including sensing displacement of the probe in response to the time-varying deformation.

2. The method of claim 1, further comprising:
varying the alternating bias voltage at a rate of about 0.01 Hz to about 1 Hz.

3. The method of claim 1, wherein the device comprises an oxide film and wherein the time-varying change in gas content of the device is a time-varying change in oxygen content of the oxide film.

4. The method of claim 1, wherein the time-varying deformation is caused by chemical expansion.

5. The method of claim 1, wherein the time-varying deformation is caused by deflection.

6. The method of claim 1, further comprising:
constraining the device while applying the time-varying stimulus.

7. The method of claim 1, further comprising:
keeping the device at a temperature of at least about 450 degrees Celsius while applying the time-varying stimulus.

8. The method of claim 1, further comprising:
filtering a signal representing the time-varying deformation based on a spectral component of the time-varying stimulus to enhance the spectral component of the time-varying deformation.

9. The method of claim 1, further comprising:
determining an amplitude of the time-varying deformation as a measure of the amount of chemical expansion or the deflection of the surface of the device.

10. The method of claim 1, further comprising:
determining a phase difference between the time-varying deformation and the time-varying stimulus as an indicator of kinetically limiting processes associated with device.

11. A system for characterizing a device, the system comprising:
a stimulus source configured to apply a time-varying stimulus to the device, the time-varying stimulus causing a time-varying change in gas content of the device, the stimulus source including a voltage source and the time-varying stimulus including an alternating bias voltage; and
a sensor including a probe in contact with a surface of the device, configured to measure a time-varying deformation of the device caused by the time-varying change in gas content of the device, the time-varying deformation based on chemical expansion or a deflection of the surface of the device induced by the time-varying change in gas content of the device, wherein the probe measures the time-varying deformation by sensing displacement of the probe in response to the time-varying deformation.

12. The system of claim 11, wherein the surface of the device comprises an oxide film and the time-varying change in gas content of the device comprises a change in oxygen content of the oxide film.

13. The system of claim 11, wherein the voltage source is configured to vary the alternating bias voltage at a rate of about 0.01 Hz to about 1 Hz.

14. The system of claim 11, wherein the sensor is configured to measure the time varying deformation based on chemical expansion.

15. The system of claim 11, wherein the sensor is configured to measure the time varying deformation based on deflection.

16. The system of claim 11, further comprising:
a heater configured to keep the device at a temperature of at least about 450 degrees Celsius during application of the time-varying stimulus.

17. The system of claim 11, further comprising:
circuitry, in electrical communication with the sensor, to filter a signal representing the time-varying deformation based on a spectral component of the time-varying stimulus.

18. A method of characterizing deformation of a device comprising an oxide film, the method comprising:
heating the device to a temperature of at least 450 degrees Celsius;
applying a time-varying voltage to the device, the time-varying voltage causing a time-varying change in oxygen content of the oxide film;
measuring, with a probe in contact with a surface of the device, a time-varying deformation of the device caused by the time-varying change in oxygen content of the oxide film, the time-varying deformation based on chemical expansion or a deflection of the surface of the device induced by the time-varying change in oxygen content of the device, the measuring including sensing displacement of the probe in response to the time-varying deformation; and
determining an amplitude of the time-varying deformation as a measure of the amount of chemical expansion or deflection; and
determining a phase difference between the time-varying deformation and the time-varying stimulus as an indicator of kinetically limiting processes associated with device.

19. A method of characterizing a device, the method comprising:
applying a time-varying stimulus to the device, the time-varying stimulus causing a time-varying change in gas content of the device, the time-varying stimulus including an alternating bias voltage;
illuminating a surface of the device; and
measuring, with a detector configured to detect light reflected off the surface of the device in response to said illuminating, a time-varying deformation of the device caused by the time-varying change in gas content of the device, the time-varying deformation based on chemical expansion or a deflection of the surface of the device induced by the time-varying change in gas content of the device, the measuring including detecting a change in the reflected light in response to the time-varying deformation.

* * * * *